United States Patent [19]

Putnam et al.

[11] Patent Number: 5,013,549
[45] Date of Patent: May 7, 1991

[54] PRODUCTION, ISOLATION, AND IDENTIFICATION OF NOVEL ANTIFUNGAL COMPOUNDS

[75] Inventors: Alan R. Putnam, Gallatin Gateway, Mont.; Saroj K. Mishra, Houston, Tex.; Muraleedharan G. Nair, East Lansing, Mich.

[73] Assignee: Board of Trustees Operating Michigan State University, East Lansing, Mich.

[21] Appl. No.: 550,070

[22] Filed: Jul. 9, 1990

Related U.S. Application Data

[63] Continuation-in-part of Ser. No. 311,299, Feb. 16, 1989.

[51] Int. Cl.$^5$ .................. A61K 31/71; C07H 15/24
[52] U.S. Cl. .................. 424/116; 424/115; 435/78; 536/6.4
[58] Field of Search .................. 424/115, 116; 435/78; 536/64

[56] References Cited

U.S. PATENT DOCUMENTS

| | | |
|---|---|---|
| 3,988,315 | 10/1976 | Umezawa et al. |
| 4,071,411 | 1/1978 | Umezawa et al. ............... 435/88 |
| 4,209,588 | 11/1980 | Umezawa et al. |
| 4,245,045 | 2/1981 | Umezawa et al. |
| 4,375,511 | 4/1983 | Fujiwara et al. |
| 4,383,037 | 7/1983 | Fujiwara et al. |
| 4,439,603 | 3/1984 | Umezawa et al. ............... 536/6.4 |
| 4,550,159 | 10/1985 | Umezawa et al. ............... 435/78 |
| 4,565,861 | 1/1986 | Umezawa et al. ............... 536/6.4 |

OTHER PUBLICATIONS

Lee, M. D. et al., J. Am. Chem. Soc. 109:3464, (1987).
Lee, M. D. et al., J. Am. Chem. Soc. 109:3466, (1987).
Golik, J. et al., J. Am. Chem. Soc. 109:3461, (1987).
White, H. B. et al., J. Biol. Chem., 243, 4517 (1960).
DeRosa, M. et al., J. Chem. Soc. Chem. Commun. p. 619 (1971).
Nair, M. S. R. et al., Tetrahedron Lett., p. 1655 (1975).
Nair, M. S. R. et al., Tetrahedron Lett. p. 1267 (1975).
Wagman, G. H. et al., Antimicrob. Agents Chemother., p. 33 (1964).
Ganguly, A. K. et al., Chem. Commun. p. 531, (1973).
Ganguly, A. K. et al., J. Am. Chem. Soc. 97, 1982 (1975).
Zahner, H. et al., J. Pathol. Microbiol. 25, 708 (1962).
Muller A. et al., Arch. Mikrobiol. 62, 250 (1968).
Bickel, H. et al., Helv. Chem. Acta, 2129 (1960).
Prelog, V. et al., Helv. Chim. Acta., 45, 631 (1962).
Bickel, H. Helv. Chim. Acta, 46, 1385 (1963).
Kondo, S. et al., J. Antibiot. (Tokyo), 30, 1137 (1977).
Kondo, S. et al., J. Antibiot. (Tokyo), 24, 732 (1971).
Oki, T. et al., J. Antibiotics, 28, 830 (1975).
Oki, T. et al., J. Antibiotics, 30, 683 (1977).
Oki, T. Jap. J. Antibiotics, 30, S70 (1977).
Oki, T. et al., J. Antibiotics, 32, 791 (1979).
Oki, T. et al., J. Antibiotics, 32, 801 (1979).
Soga, K. et al., J. Antibiotics, 770 (1971).
Tanaka, H. et al., J. Antibiotics, 34, 905 (1981).
Matsuzawa, Y. et al., J. Antibiotics, 34, 1596 (1981).

Primary Examiner—Herbert J. Lilling
Attorney, Agent, or Firm—Ian C. McLeod

[57] ABSTRACT

A new species of Micromonospora, in particular *Micromonospora spartanea* ATCC 53803, is described. The species produces antifungal compounds spartanamicins A and B. Methods for the production, isolation and characterization of the compounds are described. The compounds contain deoxy-L-fucose, as well as another hexose and an amino sugar.

11 Claims, 17 Drawing Sheets

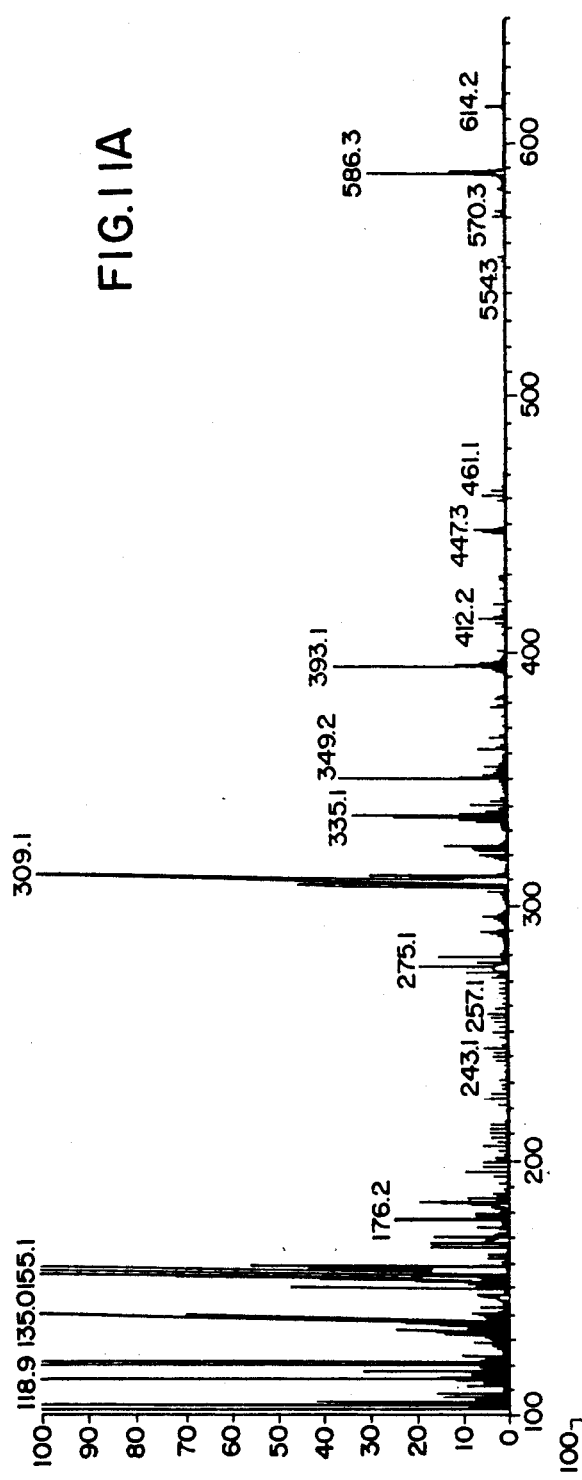
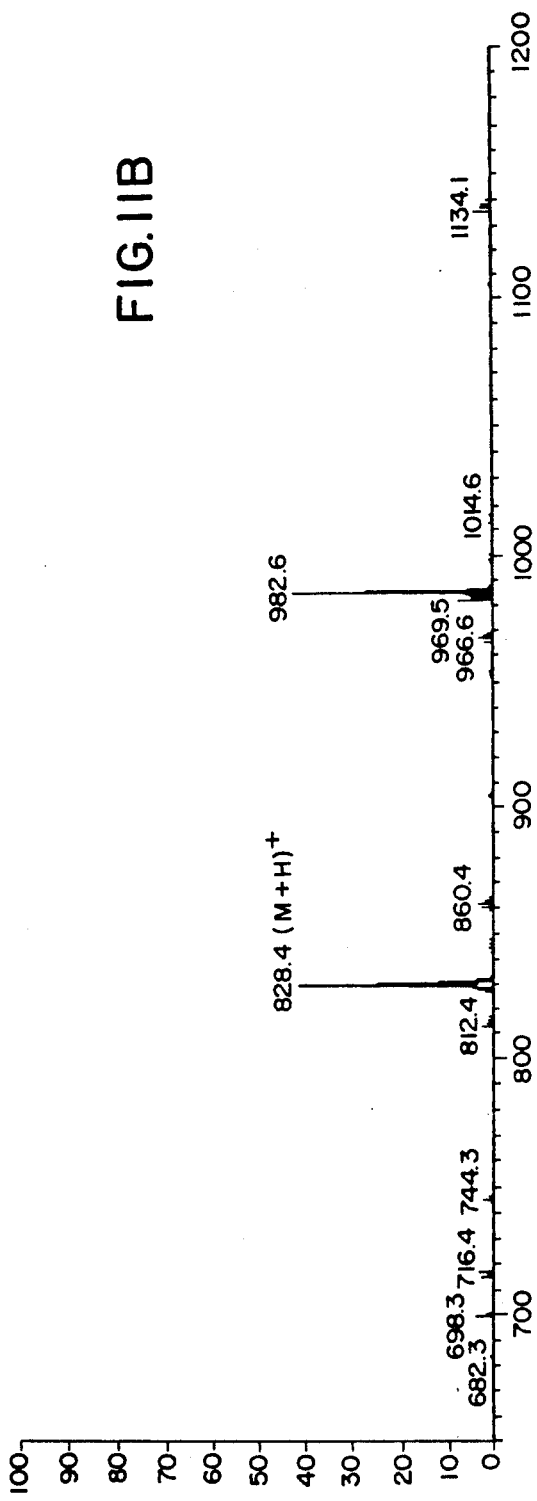

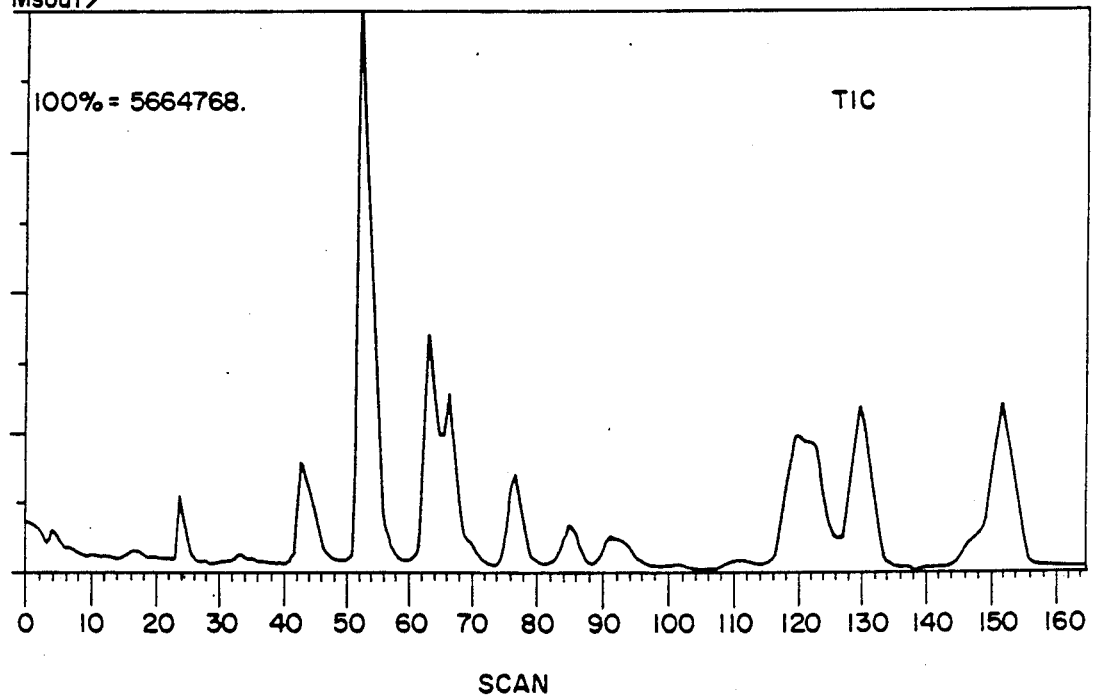

PRODUCTION, ISOLATION, AND IDENTIFICATION OF NOVEL ANTIFUNGAL COMPOUNDS

Cross Reference to Related Application

This application is a continuation-in-part of application Ser. No. 311,299, filed Feb. 16, 1989.

BACKGROUND OF THE INVENTION (1) Summary of the Invention

The present invention relates to the isolation and purification of novel potent antifungal compounds belonging to the anthracycline group of antibiotics. In particular the present invention relates to antifungal compounds produced by *Micromonospora spartanea* (ATCC 53803), a new species of Micromonospora.

(2) Prior Art

Micromonospora species are well known for their ability to produce biologically active compounds. Calicheamicin, approximately 1000-fold more active than adriamycin against murine tumors, is an unusually powerful antitumor compound isolated from *M. echinospora* ssp. Calichenis (Lee, M. D., et al., J. Am. Chem. Soc. 109:3464 (1987); Lee, M. D., et al., J. Am. Chem. Soc. 109:3466 (1987); and Golik, J., et al., J. Am. Chem. Soc. 109:3461 (1987). Triglycosidic antibiotics, isolated from *M. inositola* and *M. megalomicea* (White, H. B., et al., J. Biol. Chem., 243, 4517 (1960); DeRosa, M., et al., J. Chem. Soc. Chem. Commun. p. 619 (1971); Nair, M. S. R., et al., Tetrahedron Lett., p. 1655 (1975); and Nair, M. S. R., et al., Tetrahedron Lett. p. 1267 (1975). Other antibiotics reported from Micromonospora species are chalcidin complex, everninomicin B and D (Wagman, G. H., et al., Antimicrob. Agents Chemother., p. 33 (1964); Ganguly, A. K., et al., Chem. Commun. p. 531 (1973); and Ganguly, A. K., et al., J. Am. Chem. Soc. 97, 1982 (1975) and ferrioxamine B (Zahner, H., et al., J. Pathol. Microbiol., 25, 708 (1962); Muller, A., et al., Arch. Mikrobiol. 62, 250 (1968); Bickel, H., et al., Helv. Chem. Acta., 2129 (1960); Prelog, V., et al., Helv. Chim. Acta., 45, 631 (1962); and Bickel, H., Helv. Chim. Acta, 46, 1385 (1963).

Micromonospora spp. are also known to produce compounds similar to those obtained from Streptomyces spp. (Kondo, S., et al., J. Antibiot. (Tokyo), 30, 1137 (1977); and Kondo, S., et al., J. Antibiot. (Tokyo), 24, 732 (1971). *Streptomyces galilaeus* produces 21 anthracycline antibiotics out of which aclacinomycin A, B, and their derivatives were studied for their antitumor activities (Oki, T., et al., J. Antibiotics, 28, 830 (1975); Oki, T., et al., J. Antibiotics, 30, 683 (1977); Oki, T., Jap. J. Antibiotics, 30, S70 (1977); Oki, T., et al., J. Antibiotics, 32, 791 (1979); Oki, T., et al., J. Antibiotics, 32, 801 (1979); Soga, K., et al., J. Antibiotics, 770 (1971); Tanaka, H., et al., J. Antibiotics, 34, 905 (1981); and Matsuzawa, Y., et al., J. Antibiotics, 34, 1596 (1981). It is not known that antifungal compounds could be produced by this species.

Related patents describing anthracycline glycosides are Umezawa et al U.S. Pat. No(s). 3,988,315; 4,209,588; 4,245,045; Fujiwara et al 4,375,511 and 4,383,037.

OBJECTS

It is therefore an object of the present invention to provide antifungal compounds derived from a new Micromonospora species. It is further an object of the present invention to provide a method for the isolation of the antifungal compounds. These and other objects will become increasingly apparent by reference to the following description.

IN THE DRAWINGS

FIGS. 11 and 12 show FAB(+) and FAB(−) mass spectra for spartanamicin A and B.

Figure 16A:
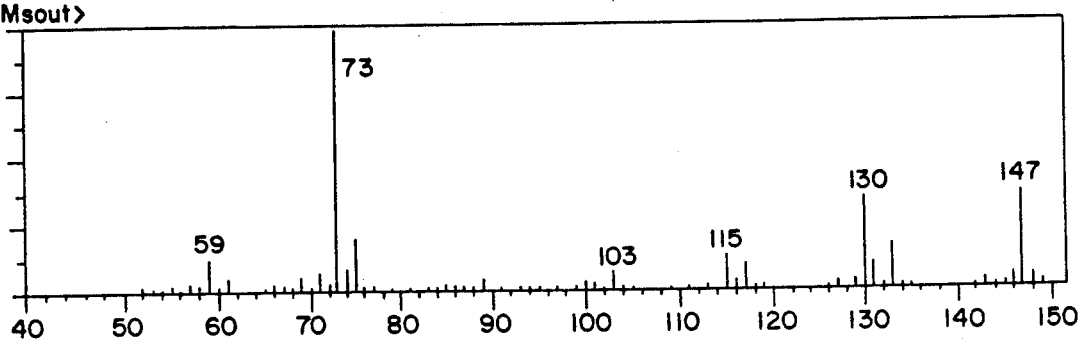
Figure 16B:
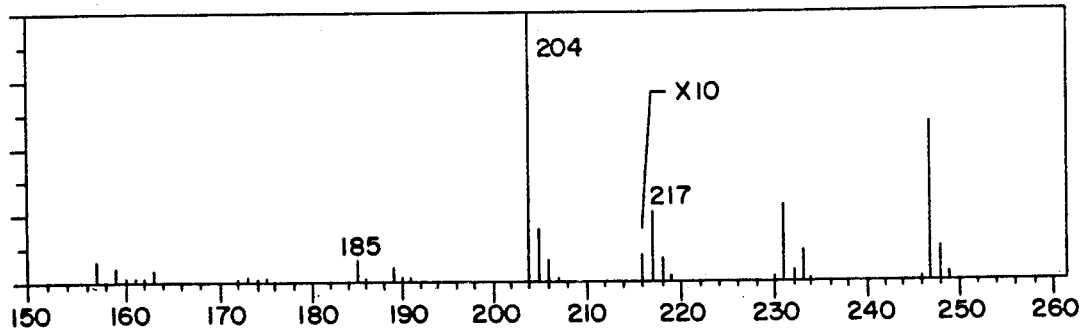
Figure 16C:
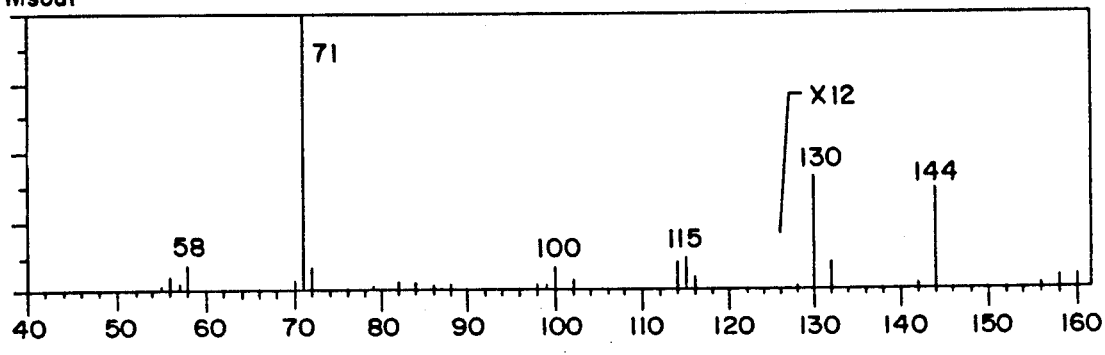
Figure 16D:
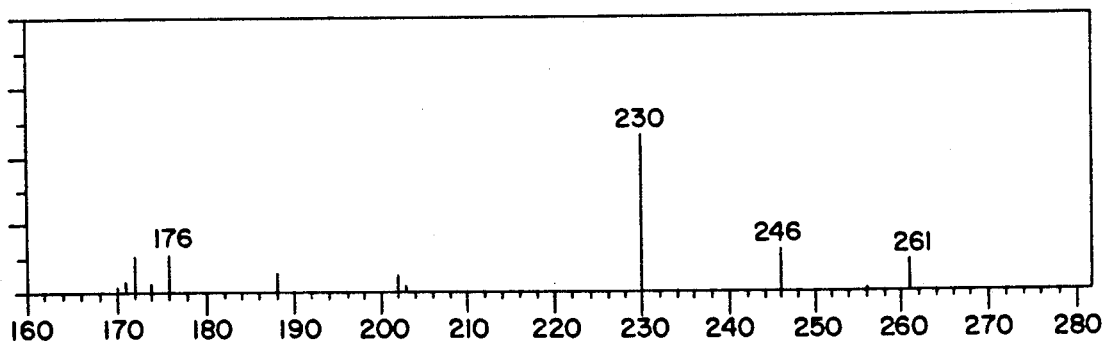

FIGS. 15 and 16 A to D show gas chromatograph mass spectra for the sugars from the hydrolysis of spartanamicin B using hydrochloric acid in methanol.

GENERAL DESCRIPTION

The present invention relates to a biologically pure culture of mycelium of *Micromonospora spartanea* ATCC 53803.

Further the present invention relates to a composition or compound, selected from the group consisting of spartanamicins A and B, having the molecular formula $C_{42}H_{53}O_{16}N$ with a molecular weight of 827 for spartanamicin B and molecular formula $C_{42}H_{51}O_{16}N$ with a molecular weight of 825 for spartanamicin A, which is produced by and isolated from mycelium of *Micromonospora spartanea* ATCC 53803.

Further the present invention relates to a method for producing an antifungal composition which comprises: culturing mycelium of *Micromonospora spartanea* deposited as ATCC 53803 in a growth medium; isolating the mycelium of the *Micromonospora spartanea* from the growth medium; and contacting the mycelium, which are preferably disrupted, with an organic solvent for the spartanamicins which is a non-solvent for the mycelium; and isolating the spartanamicins from the solvent as a composition with impurities.

The present invention relates to a compound having an aglycone of the formula:

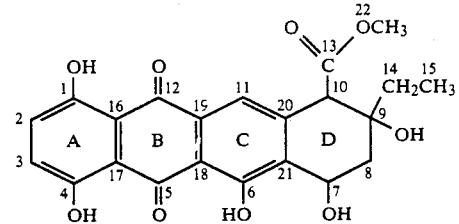

upon hydrochloric acid hydrolysis in methanol and sugar residues of deoxy-L-fucose, a hexose and an amino sugar which is a hexose by proton and carbon NMR gas chromatograph mass spectroscopy and the same sugar residues upon collisionally induced disassociation using mass spectroscopy.

Finally the present invention relates to a compound having a formula selected from the group consisting of $C_{42}H_{53}O_{16}N$ with a molecular weight of 827 and referred to as spartanamicin B and $C_{42}H_{51}O_{16}N$ with a molecular weight of 825 and referred to as spartanamicin A and each compound having an aglycone of the formula:

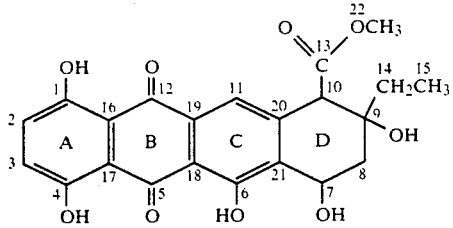

upon acid hydrolysis and for spartanamicin B sugar residues of rhodosamine, deoxy-L-fucose and spartanose and for spartanamicin A sugar residues of deoxy-L-fucose, rhodosamine and cinerulose by gas chromatograph mass spectroscopy and the same sugar residues upon collisionally induced disassociation of spartanamicin A and B using mass spectroscopy.

Spartanamicin A and B are structurally similar to the cinerubins A and B produced by *Streptomyces capoamus* and 1-hydroxy MA144M1 produced by *Streptomyces galilaeus*; however, these compounds are not significantly antifungal. The compounds of the present invention have very significant antifungal properties and are therefore believed to be stereoisomers. The cinerubins are soluble in methanol and ethanol while spartanamicin A and B are not soluble in these solvents.

The growth medium for the production of spartanamicin A and B includes yeast extract, maltose and D-glucose as essential ingredients, preferably 4 grams yeast extract, 10 grams maltose, and 4 grams glucose per liter of water. Several media, including these ingredients which produced the orange-red pigmentation, were satisfactory. The preferred medium produced 30 to 60 mg/liter of culture broth for spartanamicin B and 18 to 30 mg/liter of culture broth for spartanamicin A. These results are with the wild strain and yield can be improved with strain improvement. Compounds A and B are then extracted from the mycelium of the *Micromonospora spartanea* ATCC 53803.

An extraction solvent is selected which dissolves the spartanamicins A and B but which is a non-solvent for the mycelium of the Micromonospora spartanea. Such solvents are for instance chloroform, dichloromethane, ethanol, propanol, isopyranol, butanol, ethylacetate, and carbon tetrachloride.

The spartanamicins A and B can be purified using chromatographic methods well known to those skilled in the art. Such methods can include affinity, ionic or reverse phase chromatography, for instance. Preferred is solid phase extraction under vacuum using column silica, flash column chromatography using silica and final purification by preparative TLC using tapered thin layer plates (2000 microns).

The spartanamicins A and B can be used to inhibit microorganisms, particularly fungi and bacteria. The amount used is sufficient to inhibit the growth of the microorganism, preferably between about 0.1 and 1.0 micrograms per milliliter. The dosages can contain between about 0.01 and 400 micrograms per liter. Growth of the micoorganisms can be inhibited or in certain instances they can be killed.

The spartanamicins A and B can be mixed with a pharmaceutically acceptable carrier for administration by various routes, such as by parenteral, intravenous and subcutaneous routes. The carrier can be a pill form, powders, aerosol spray or any other therapeutically acceptable delivery system which provides a therapeutically effective dosage.

SPECIFIC DESCRIPTION

EXAMPLE 1

This example describes the isolation and taxonomy of *Micromonospora spartanea* ATCC 53803.

(*Micromonospora spartanea* sp. novo, strain 43097) which was isolated from a soil sample collected from the rhizosphere of an indoor potted asparagus plant. It is deposited with the American Type Culture Collection in Rockville, Md. under the Budapest Tr aty.

One g of the soil was vortexed with 9 ml of physiological saline (0.85% NaCl in distilled water) and serial dilutions prepared. A 0.1 ml of the suspension was uniformly spread on the surface of N.Z. amine-A agar (N.Z. amine-A 3 g, bacto agar 18 g, Tap water 1 l) fortified with nystatin (0.03 g/l) and cycloheximide (0.5 g/l) and contained in disposable sterile plastic petri-dishes having a diameter of 100 mm. The inoculated petri-dishes were packed in a plastic bag and incubated at 26° C. for two weeks. A small (about 2 mm in diameter) reddish-pink colony, spotted at this stage was picked up and subcultured on slanted YMG agar (yeast extract 4 g, malt extract 10 g, glucose 4 g, bacto agar 20 g and distilled water 1 l, pH 6.8) and incubated at 26° C. After checking purity of the culture, it was processed for various biological activities and taxonomic characteristics.

Antifungal Activities

Initially, the cultures were grown in 500 ml baffled bottom erlenmeyer flasks containing 100 ml liquid YMG medium (same as above but devoid of agar) and placed on a rotary shaker (200 rpm) at 26° C. After a week, the flasks were removed from the shaker and 0.03 ml of the culture broth was placed in the center of a petri-dish containing 20 ml Emmon's Sabouraud agar (neopeptone 10 g, glucose 20 g, bacto agar 20 g, distilled water 1 l, pH 6.8) seeded with ca $10^4$ C.F.U. of the test organism. An equal amount of the uninoculated culture medium was placed at a corner of the petri-dish as control. During the initial screening the test organisms included yeast phase of *Candida albicans* and conidia of *Aspergillus fumigatus*. The petri-dishes were incubated at 26° C. for 48 hours, thereafter a clear zone of inhibition characterized by absence of the growth of the test organism around the broth droplet, was measured.

Taxonomy of the Producer Strain

Strain 43097 grows well on most of the YMG, Bennett's and Emmon's agars. On YMG agar, the growth after two to three days is orange with a pinkish center which attains a diameter of about 3–5 cm after a week and develops intense ruby-red color. As the colony gets older, the color becomes more intense with a pinkish hue. After 4 to 6 weeks, the colonies develop light to medium brown crest which is more marked in the center. Production of diffusible pigment is negligible or absent. Production of aerial hyphae is rarely observed. When present, white, long filaments of the scanty aerial hyphae are visible in 6 to 8 weeks old cultures. Microscopically, the substrate hyphae are well developed and show extensive branching. The filaments are Gram positive, usually with beaded appearance, but not acid fast. They are less than one micron in width. Sporulation is scanty, usually observed in older cultures (4 to 6 weeks); the spores are produced singly, they could be lateral or terminal, borne on a small sporophore. Sporangia and arthrospores are never seen. A study of physiological and biochemical characteristics (Gordon tests) revealed following properties:

Strain 43097 decomposes adenine, tyrosine, casein, urea and hypoxanthine It hydrolyzes starch and produces nitrite from nitrate. The strain is sensitive to lysozyme. It produces acid with arabinose, cellubiose, glucose, glycerol, galactose, inositol, lactose, maltose, melibiose, methyl-D-glucoside, raffinose, rhamnose, trehalose, xylose, but not with adonitol, erythritol, mannitol, melzitose, and sorbitol. Glycine was the major product observed during the chemotaxonomic analyses of the whole cell hydrolysate.

A search of published reports concerning the taxonomy of Micromonospora species revealed that the aforementioned characteristics are not compatible with the morphological and physiological properties of any of described species. Type or neo-type cultures of 40 (almost all the hitherto described) species of Micromonospora were obtained and a comparative study of their morphological and physiological characteristics was performed. The properties of strain 43097 though comparable to the extent that it can be given the generic name Micromonospora, are very distinct and cannot be compared with any of the species examined. The new species name, spartanea is proposed to accommodate strain 43097 and other isolates with similar properties.

Different media used for the growth of 43907 and Spartanamicin A and B production are listed below:

| Medium No. | Components of the Medium in g/l | | Remarks |
|---|---|---|---|
| I | D-glucose | 20 | |
| | Soluble starch | 20 | Good growth |
| | Peptone | 5 | Little or no com- |
| | Yeast Extract | 2.5 | pounds of interest |
| | $K_2HPO_4$ | 1.0 | produced. |
| | $MgSO_4$ | 1.0 | |
| | NaCl | 3.0 | |
| | $CaCO_3$ | 3.0 | |
| II | D-glucose | 20 | Good growth |
| | Soluble starch | 20 | Little or no com- |
| | Yeast extract | 5 | pounds of interest |
| | $MgSO_4$ | 1.0 | produced. |
| | NaCl | 3.0 | |
| | $CaCO_3$ | 3.0 | |
| III | Yeast Extract | 4 | Good growth |
| | Maltose | 10 | Red orange color |
| | D-glucose | 4 | Little or no |
| | Soluble Starch | 20 | Spartanamicin B. |
| | $MgSO_4$ | 1.0 | Very little |
| | NaCl | 3.0 | Spartanamicin A. |
| | $CaCO_3$ | 3.0 | |
| IV | D-glucose | 20 | Good growth |
| | Soluble Starch | 20 | |
| | Pharma medium | 10 | No compounds of |
| | $MgSO_4$ | 1.0 | interest |
| | NaCl | 3.0 | production |
| | $CaCO_3$ | 3.0 | |
| V | Actinomycetes broth contain the following | 57 | Good growth |
| | Bacto heart infusion broth | 25 | No red orange color, |
| | Bacto yeast extract | 5 | or any pigment |
| | Bacto custone | 4 | production |
| | Cysteine HCl | 1 | |
| | Bacto Dextrose | 5 | |
| | Soluble Starch | 1 | |
| | $KH_2PO_4$ | 15 | |
| | $(NH_4)_2SO_4$ | 1 | |
| | $MgSO_4$ | 0.2 | |
| | $CaCl_2$ | 0.02 | |
| VI | Peptone | 5 | Good growth |
| | D-glucose | 10 | No production of |
| | Molasses | 20 | spartanamicins |
| VII | Yeast Extract | 4 | Good growth |
| | Maltose | 10 | Maximum yield of |
| | D-glucose | 4 | Spartanamicins |
| VIII | Neopeptone | 10 | Good growth |
| | D-glucose | 20 | No production of Spartanamicins |
| IX | Pharma Media | 5 | Good growth |
| | Molasses | 10 | Little or no |
| | Proflow oil | 5 | production of |
| | Dextrin | 10 | Spartanamicins |
| | NZ-amine-A | 5 | |

EXAMPLE 2

This Example describes the production and isolation of spartanamicin A and B.

Growth Conditions for *Micromonospora spartanea*

It was grown in shake culture (130 rpm) at 26° C. in 2 l baffle-bottomed erlenmeyer flasks containing 400 ml of a medium composed of yeast extract (4 g/l), maltose 10 g/l) and glucose 4 g/l). The medium after sterilization had a pH 6.5-7.0 and was incubated with 2 ml of a suspension of pulverized colonies. Within the 2-5 day incubation period the medium became orange red and within 5/7 days, deep red. Upon the production of this orange red pigment, the mycelium was harvested by cold centrifugation (10,000 rpm, 10 minutes) followed by vacuum filtration through a sintered glass filter (fine). The red orange mycelium was vacuum dried to remove as much broth as possible followed by extraction of spartanamicins.

Isolation and Purification of Spartanamicins A and B

Figure 1:
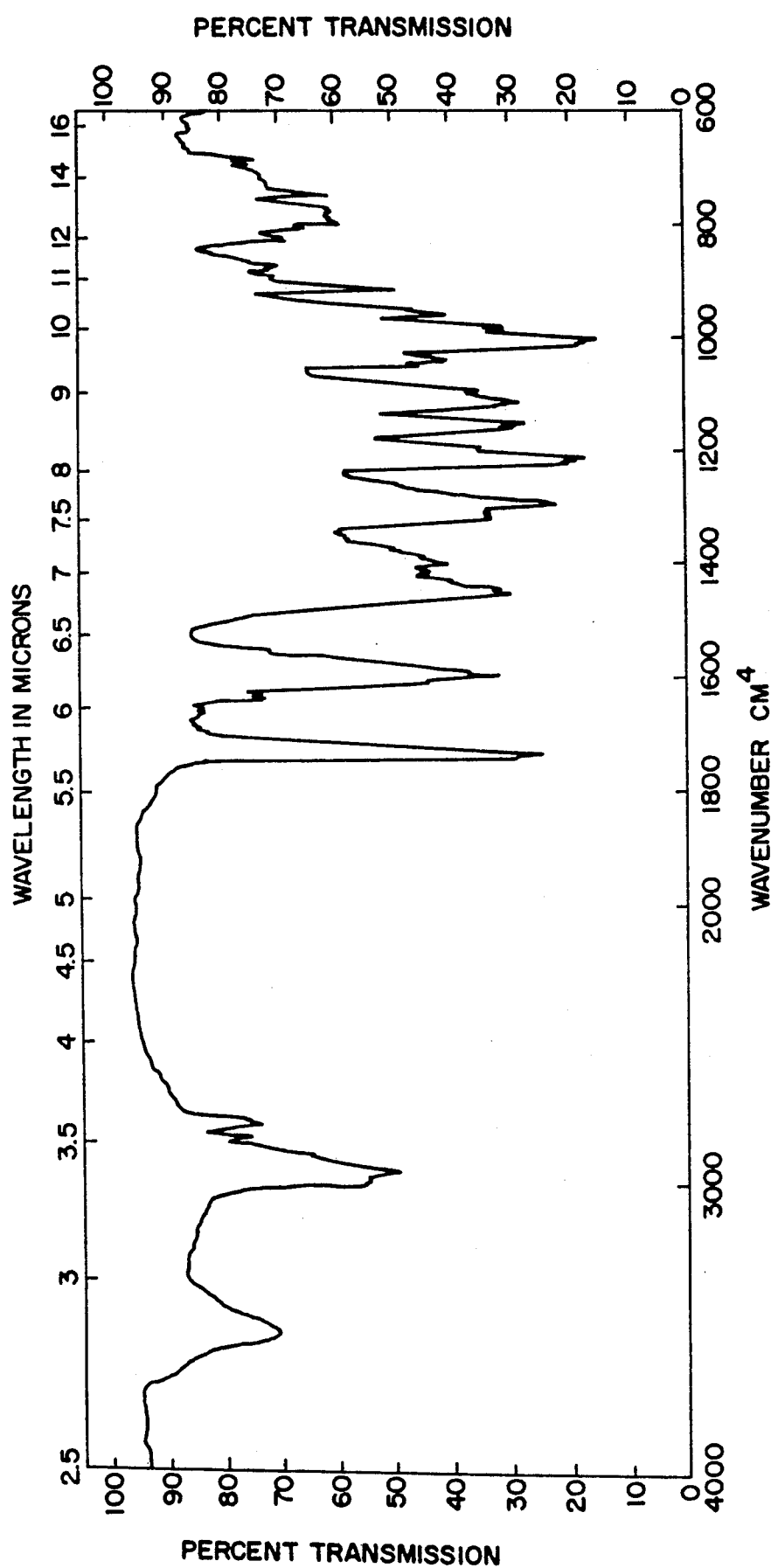
FIGS. 1 and 2 show infrared spectra for spartanamicin A and B.
Figure 2:
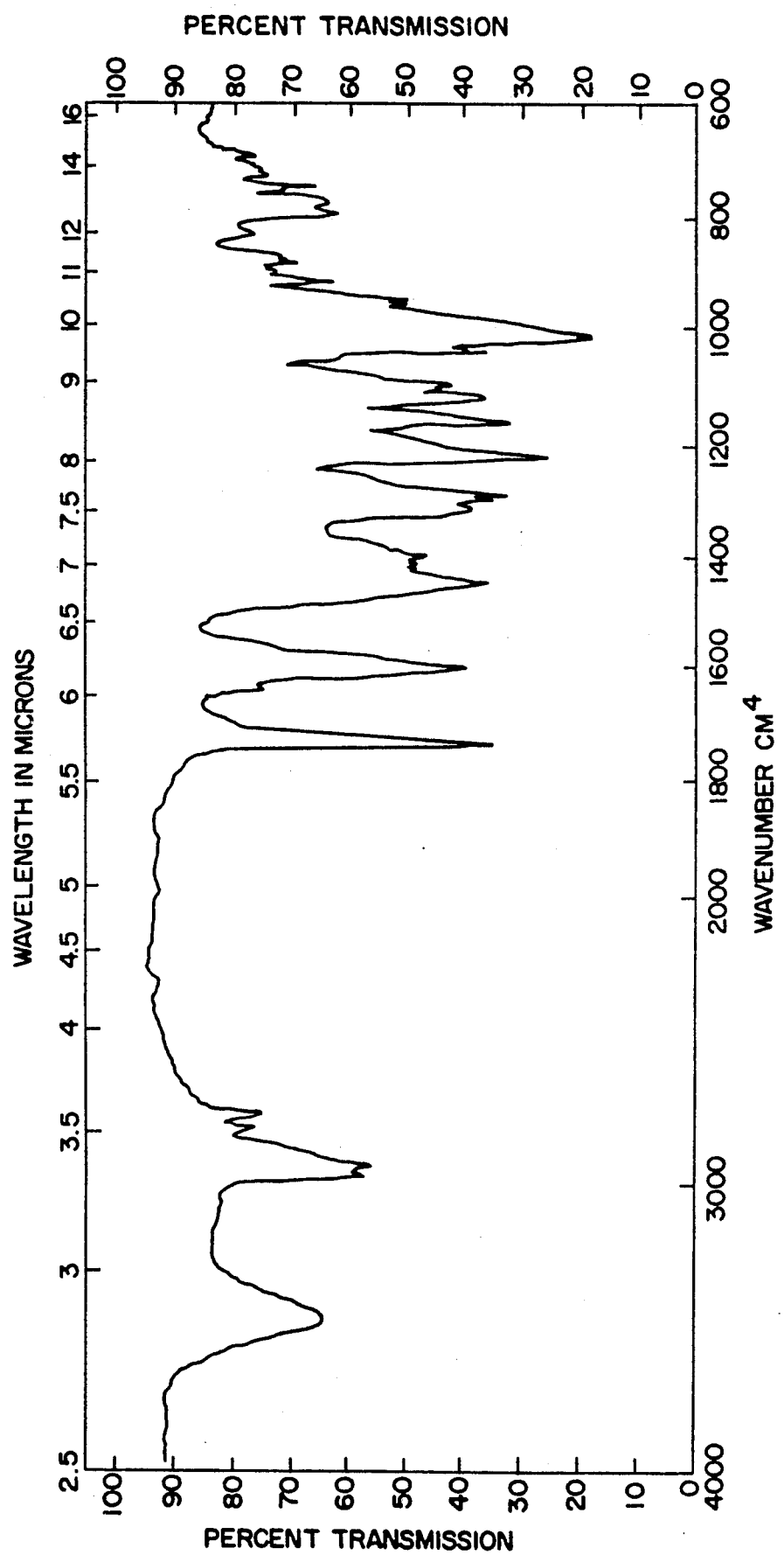
Figure 3:
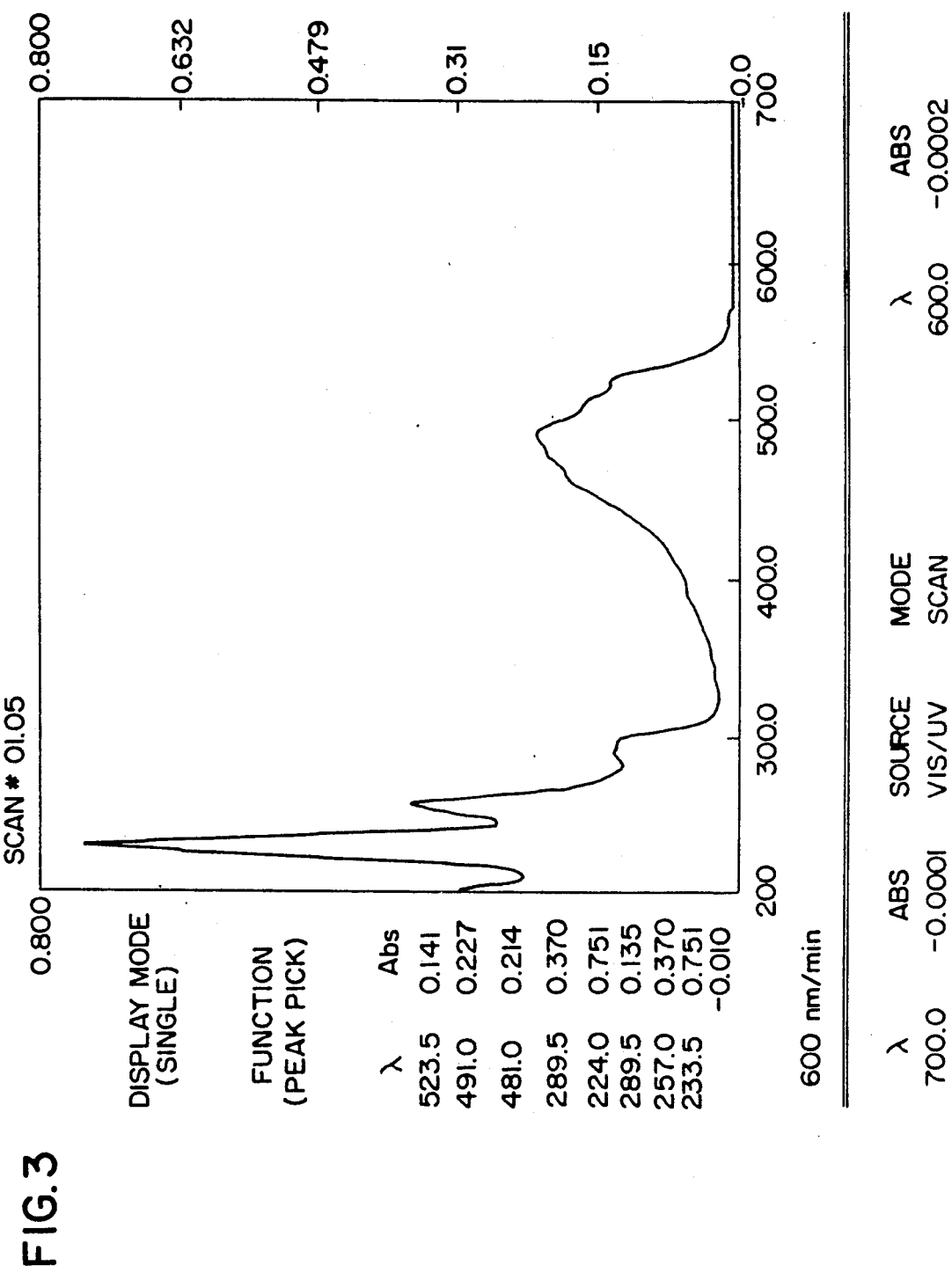
FIGS. 3 to 8 show UV spectra for spartanamicin A and B.
Figure 4:
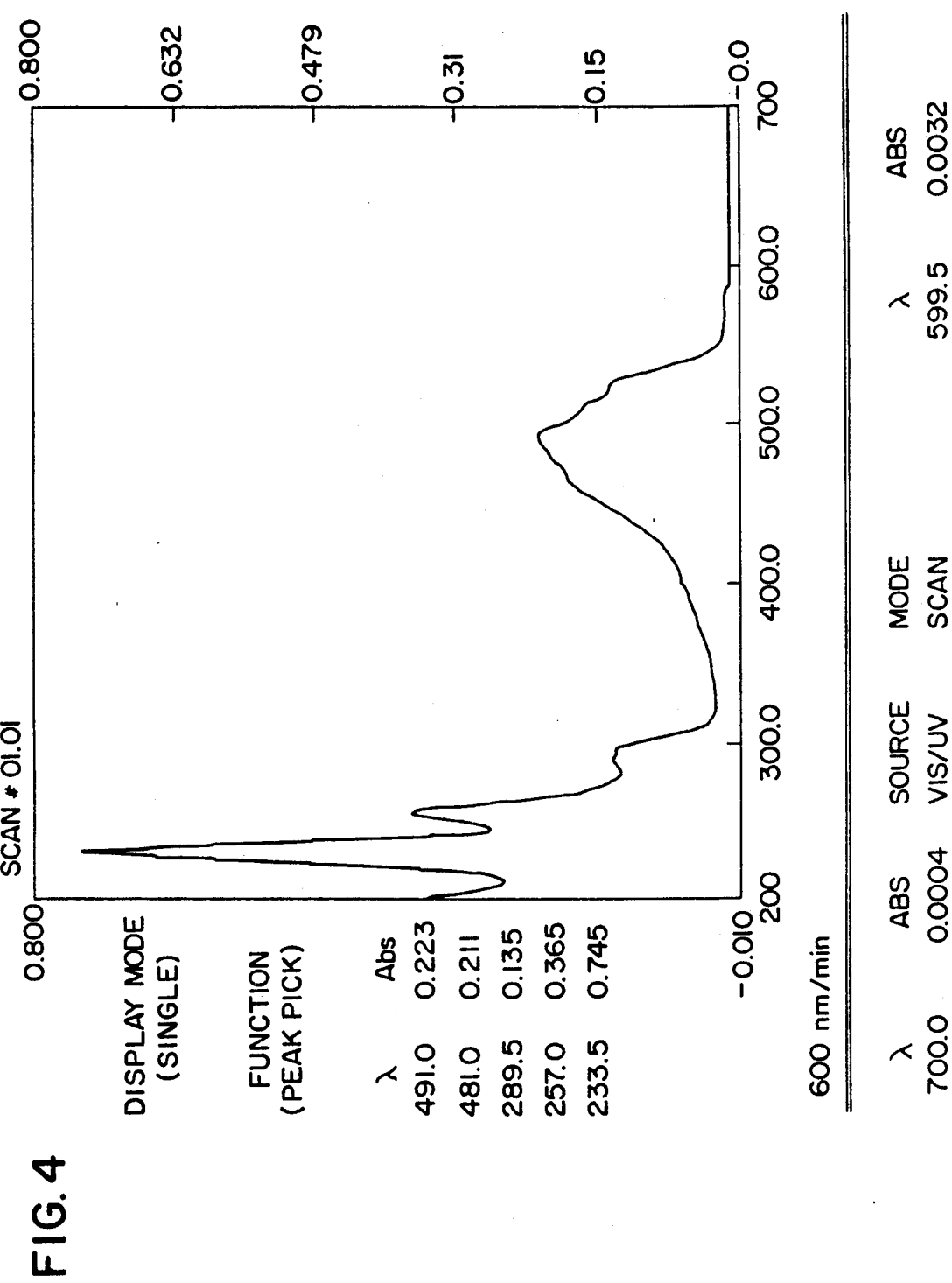
Figure 5:
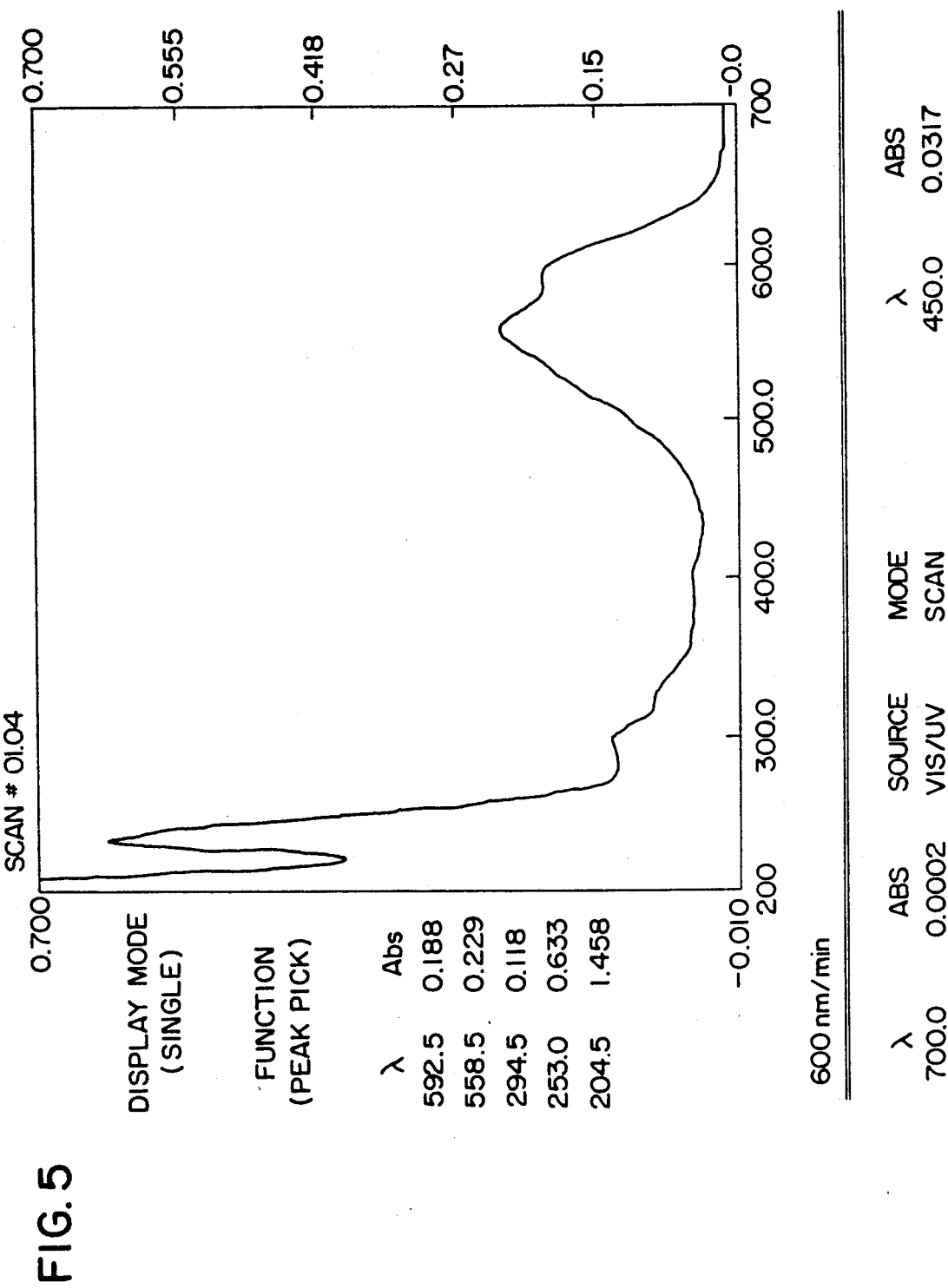
Figure 6:
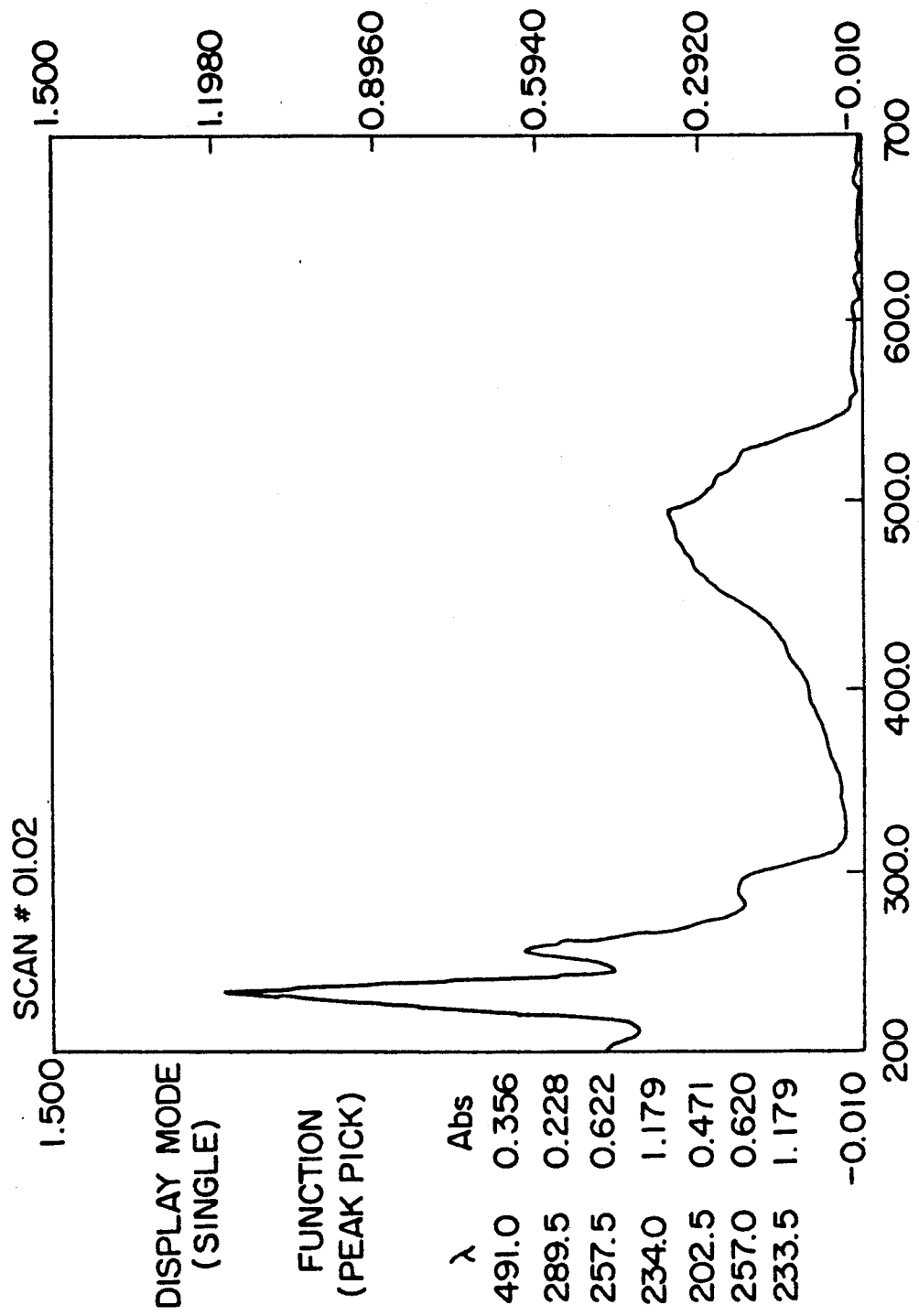
Figure 7:
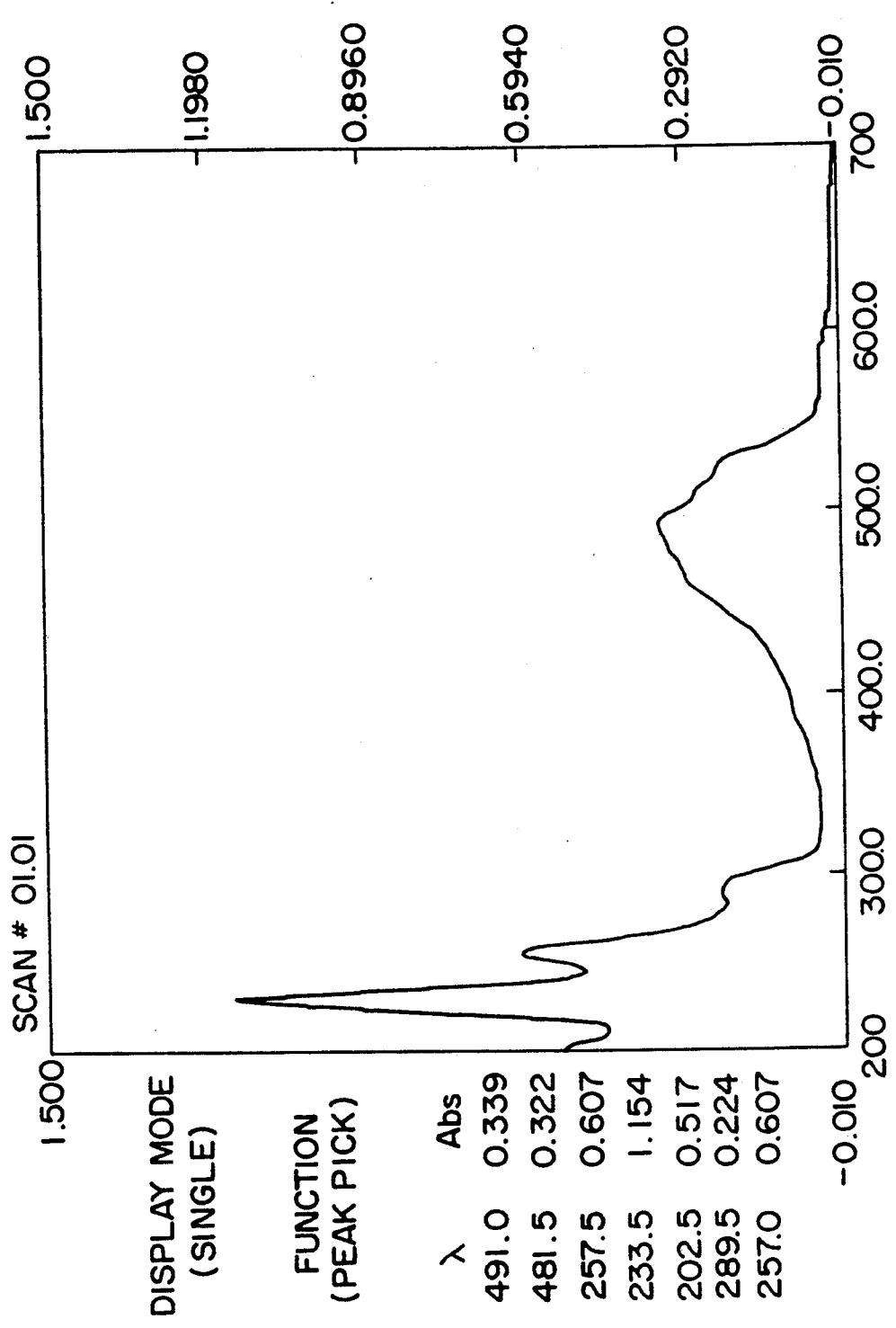
Figure 8:
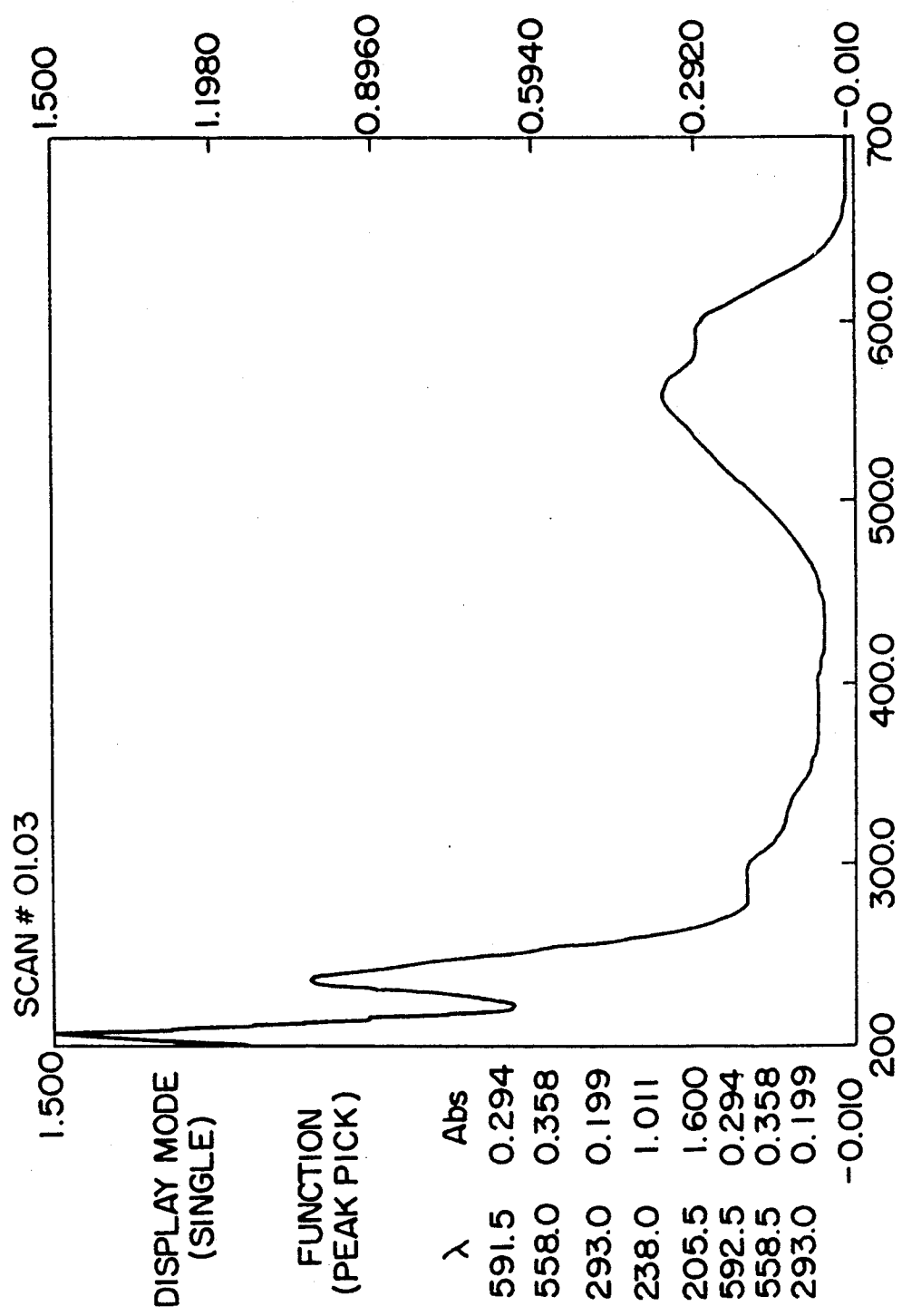
Figure 9:
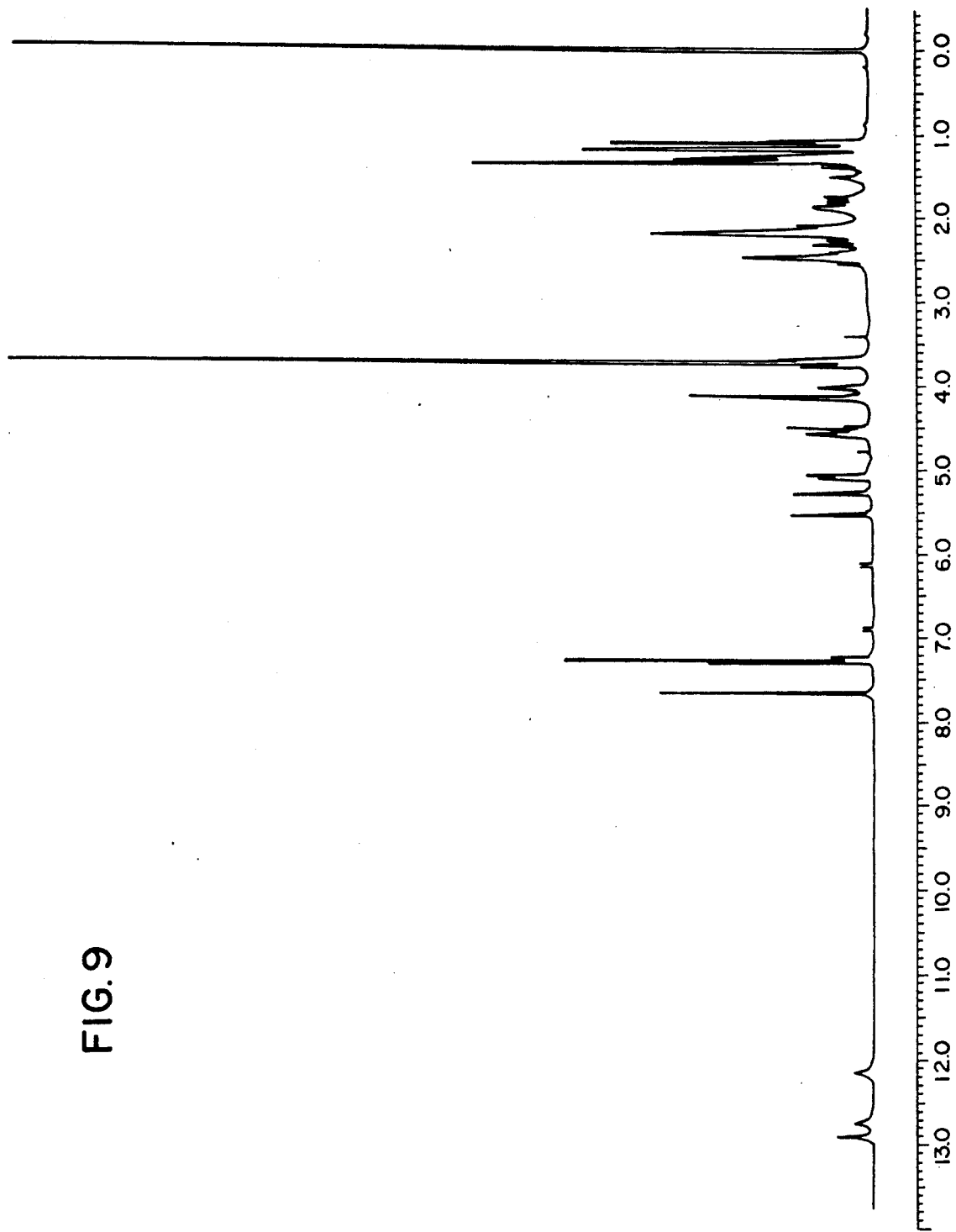
FIGS. 9, 10, 13 and 14 show the NMR spectra for spartanamicin A and B.
Figure 10:
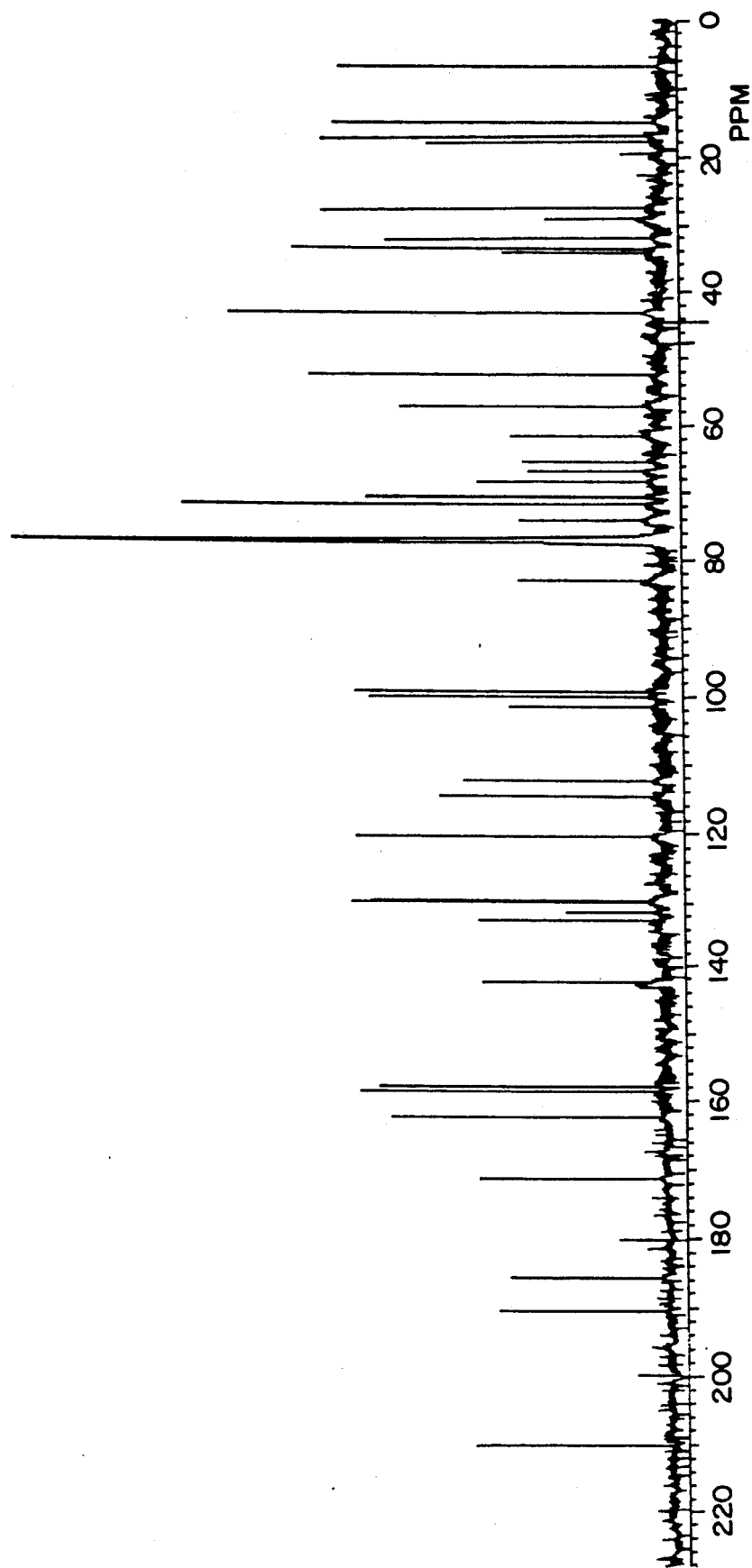
Figure 12A:
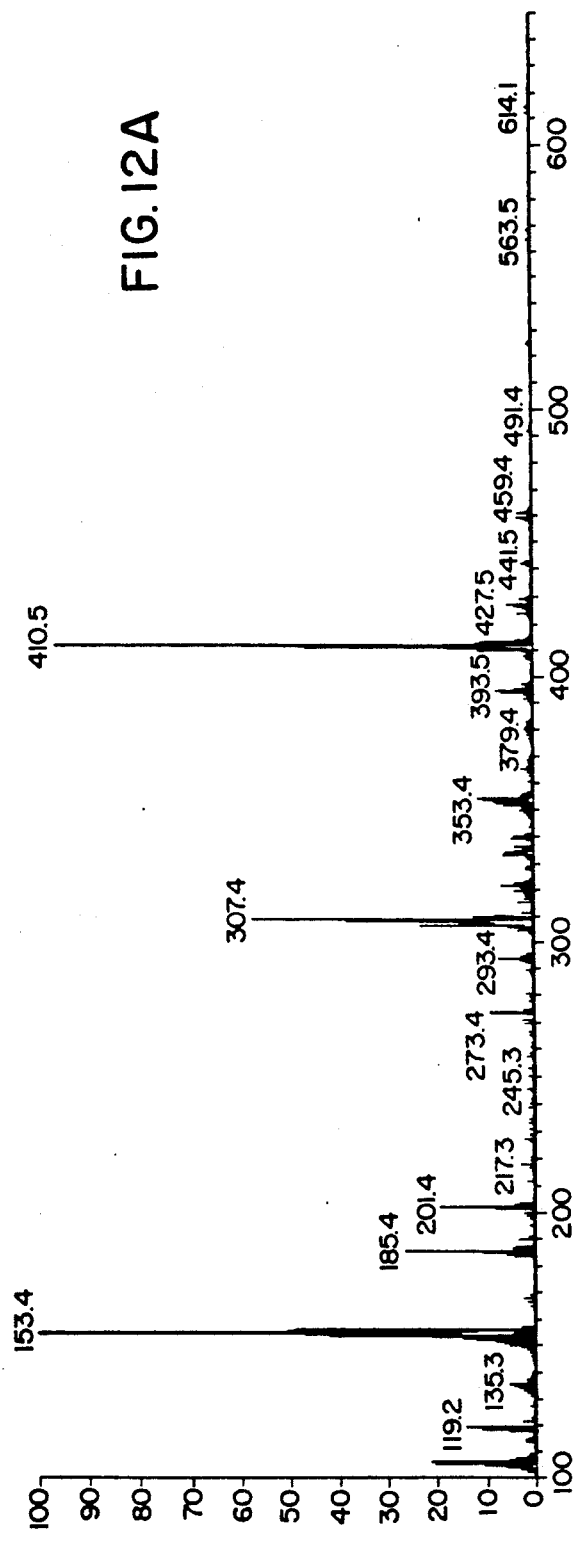
Figure 12B:
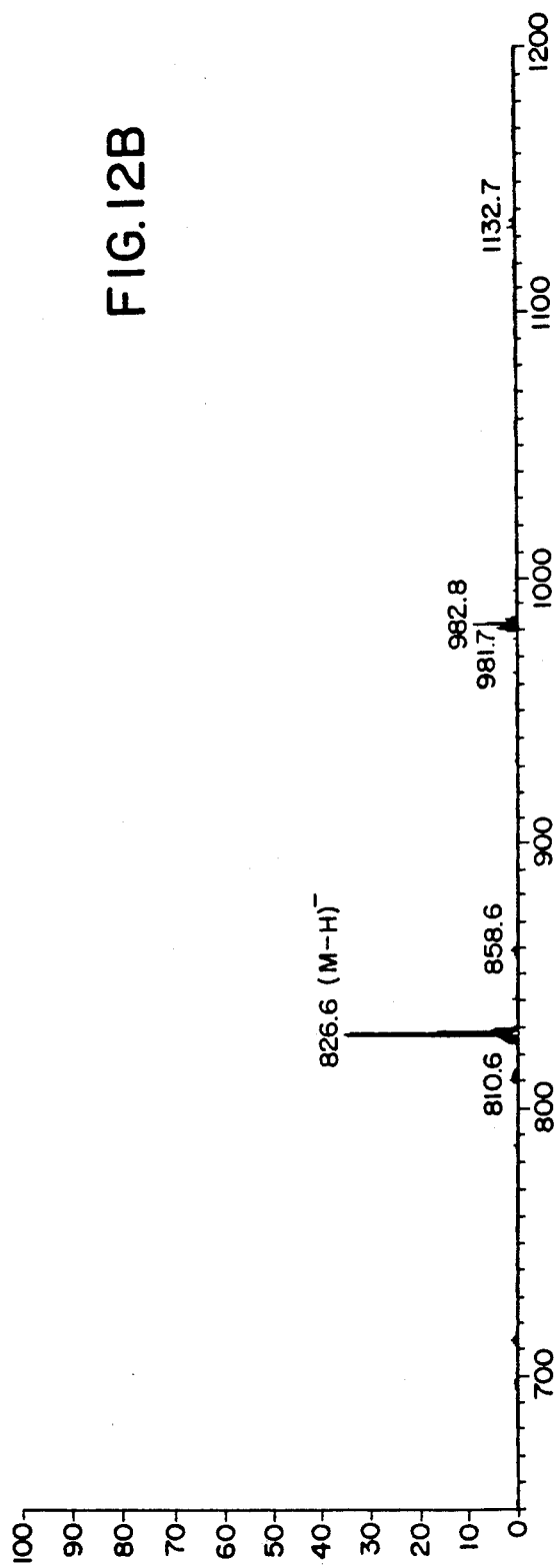
Figure 13:
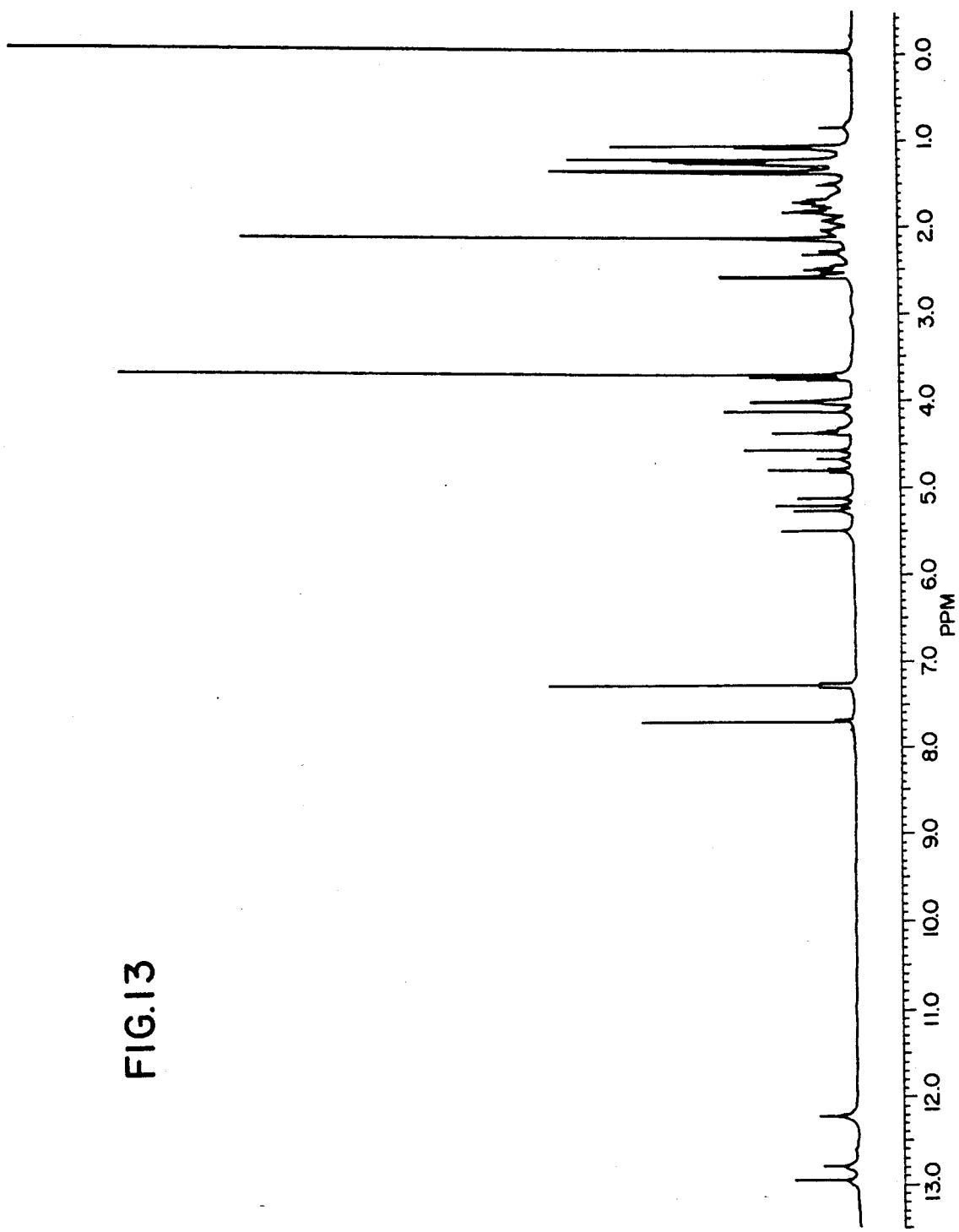
Figure 14:
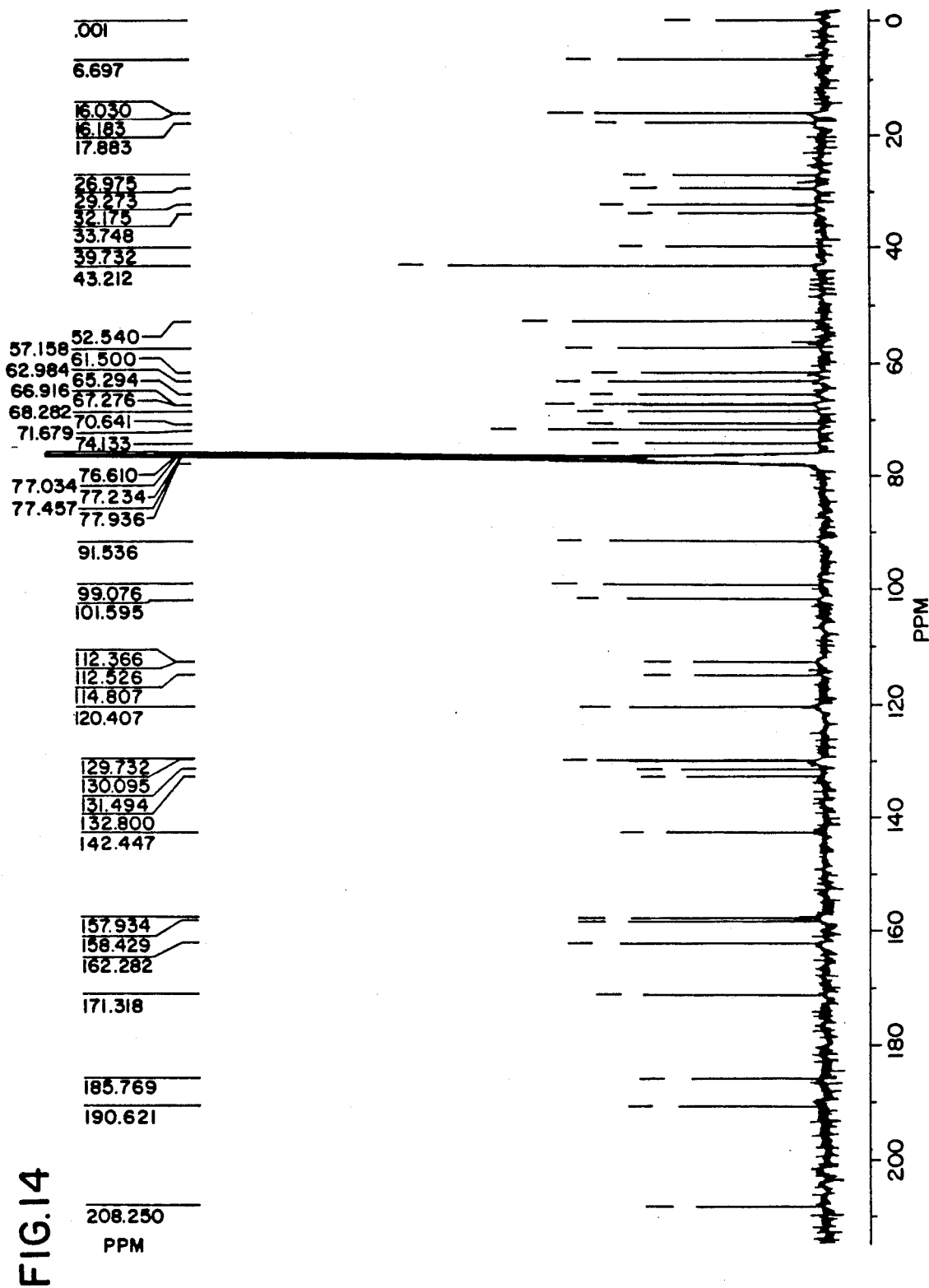

The mycelium (135 g, fresh weight) was homogenized with $CHCl_3$-MeOH (4:1 v/v, 3 l) for 5 minutes and filtered through sintered glass funnel (fine). The residue in the funnel was washed with the above solvent system (200 ml). The combined filtrate was evaporated to dryness in vacuo at 40° C. The reddish crude extract (4.6 g) was initially purified by solid phase extraction under vacuum as follows: A sintered glass filter (fine, 250 ml) containing column silica (160 g) and fitted with a buchner flask was connected to a water pump vacuum line. Under vacuum, a solution of the crude extract in $CHCl_3$ was applied on the surface of the silica and extracted with pure $CHCl_3$ (500 ml). This was followed by $CHCl_3$-MeOH (16:1 v/v) and the fractions were collected in three 500 ml portions. After a TLC check of the fractions, the $CHCl_3$ and the third fraction of the $CHCl_3$-MeOH extraction was discarded. The two remaining fractions were combined and dried at the rotary evaporator. The red amorphous solid thus obtained (1.2 g) was finally purified by preparative TLC using tapered silica plates (2000 microns, 12 plates) and $CHCl_3$-MeOH (16:1 v/v) solvent system. Two biologically active bands, determined previously by TLC bioassay, at Rf 0.48 and 0.72 were collected and eluted with the same solvent system and evaporated under reduced pressure. The band at Rf 0.48, a red solid, precipitated from $CHCl_3$-Hexane mixture, afforded an orange red powder (300 mg), spartanamicin B. This compound gave only one spot by TLC and was spectroscopically pure (FIGS. 1 to 14). The band at Rf 0.72 processed as above also gave a red orange powder, spartanamicin A (150 mg).

TLC Bioassay for the Detection of the Biological Activity

The crude extract obtained from the mycelium was spotted on a TLC plate (5×20, 0.2 micron) and developed (CHCl$_3$-MeOH, 16:1 v/v). The plate was then marked under UV and visible light for individual spots or regions. The spores of the agar slant culture of the test organism was suspended in 10 ml of sterile physiological saline. The growth medium containing agar was then shaken well with 50 ul of the above suspension (35–40° C.) and poured over the developed TLC plate uniformly and allowed to set. The plates were then placed in a moist chamber and incubated at 26° C. for 24 to 72 hours and the zone of inhibition was recorded for the respective spots of the plate. The test organisms were *Candida albicans*, *Aspergillus fumigatus*, and *Cladosporium* spp. fungi and the growth medium was potato dextrose agar (PDA, 39 g/l).

HPLC Separation of Spartanamicins

The spartanamicin complex (5 ug) and 0 spartanamicin B (5 ug) were subjected to high performance liquid chromatography. The column was a NovaPak silica (3.9×160 mm) and the mobile phase was CHCl$_3$:MeOH:Formic acid (50:48:2). The flow rate was 1.5 ml/min. Compounds were detected with a UV-Vis detector at 490 mm. The spectra under various conditions are shown in FIGS. 3 to 8.

EXAMPLE 3

This example shows the antifungal activity of the separated spartanamicins A and B.

Minimum Inhibitory Concentration

Known amounts of the purified substance were dissolved in DMSO and serial dilutions prepared in the same solvent. A 20 ul volume of each dilution was placed on the surface of Emmon's agar in petri-dishes seeded with various test strains of pathogenic and saprophytic fungi. The antibacterial activity was monitored using Muller-Hilton agar. The minimum inhibitory concentration (MIC) was determined by incorporating known amount of the DMSO dissolved purified substance into Emmon's liquid medium (same as stated earlier but devoid of agar) contained in test tubes. The tubes were inoculated with ca 2×10$^3$ CFU of the test organisms. The inoculated tubes were incubated at 26° C. and the results recorded after two to 5 days depending upon the growth pattern of the test organisms (certain fungi grow faster than others). Tubes inoculated in an identical manner but devoid of the active substance served as controls. MIC was the lowest concentration required to completely inhibit growth of the test organisms. Results currently available are presented in Table 1.

| Organisms | MIC (ug/ml) |
| --- | --- |
| Aspergillus fumigatus | 0.4 |
| A. niger | 0.6 |
| A. flavus | 0.6 |
| Penicillium species | 0.2 |
| Cladosporium species | 0.4 |
| Candida albicans | 0.2 |
| C. quilliermondii | 0.8 |
| Cryptococcus neoformans-N-2 | 0.8 |
| C. neoformans- N-3 | 0.6 |
| C. neoformans- G-3 | 1.0 |
| C. neoformans serotype-C | 0.8 |
| C. neoformans serotype-D | 0.8 |
| Rhodotorula rubra | 0.8 |
| R. glutinis | 0.4 |
| Citrobacter species* | not active |
| Pseudomonas aeruginosa* | 100 |
| Plebsiella pneumoniae* | 100 |
| Escherichia coli* | not active |
| Staphylococcus aureus ATCC 29213* | 0.8 |
| S. aureus ATCC 25923* | 0.8 |
| S. aureus (multiple drug resistant)* | not active |

N = encapsulated, mucoid strains with neurotropic tendencies
G = non-encapsulated, dry-pasty, highly virulent strain.
* = Bacterial strains; all others are fungi.

EXAMPLE 4

This Example describes the characterization of the separated spartanamicins A and B. The infrared spectra, UV spectra, NMR and mass spectral results are shown in FIGS. 1 to 14.

Characterization of Spartanamicins

Spartanamicin B

Red orange amorphous solid, C$_{42}$H$_{53}$O$_{16}$N (Calcd: 827.3453, found: 826.3448); mp. 159–161° C.; IR (KBr): 3463, 2939, 1736, 1601, 1452, 1295, 1010 cm$^{-1}$; UV (MeOH—H$_2$O, pH=7.42) ($\epsilon$): 491 (11821), 481 (11185), 289 (7156), 257 (19349), 253 (39494), UV (MeOH—H$_2$O, pH=1.46) ($\epsilon$): 523 (7474), 491 (12033), 481 (11344), 289 (7156), 257 (19614), 234 (39812); UV (MeOH—H$_2$O, pH=12.36) ($\epsilon$): 592 (9401), 516 (11000), 496 (14511), 488 (13497), 486 (13458), 297 (8816), 290 (8855), 258 (22001), 240 (22781); $^1$H— and $^{13}$C—NMR (Tables 2 and 3); MS (FAB+, % intensity): 828 (55, C$_{42}$H$_{54}$O$_{16}$N, M$^+$+H), 698 (10), 614 (10), 586 (50, C$_{30}$H$_{34}$O$_{12}$), 393 (100, C$_{22}$H$_{17}$O$_7$), 349 (30, C$_{21}$H$_{17}$O$_5$); MS (FAB—; intensity): 826 (45, M—H), 810 (5), 614 (5), 410 (100), 307 (60); MS (FAB+, CID, % intensity): 828 (100), 698 (10), 614 (7), 586 (100), 418 (7), 393 (70), 349 (60); MS (CI positive, % intensity): 828 (10), 810 (5), 586 (5), 418 (10), 392 (100), 377 (15), 361 (20).

Spartanone, the Aglycone from Spartanamicin B

Spartanamicin B (100 mg) was dissolved n HCl in MeOH (5 N, 10 ml) and kept at room temperature (1 hr). A TLC check of the reaction mixture showed the disappearance of the starting material. It was dried in vacuo and purified by TLC (silica plate, 16:1 CHCl$_3$-MeOH). Elution of the orange band and removal of the solvent at reduced pressure afforded a reddish amorphous powder which was then crystallized from CHCl$_3$-Hexane. The resulting red orange and plate like product, spartanone (50 mg) had mp. 248–249° C.; UV (MeOH), ($\epsilon$): 201 (15756), 233 (38894), 257 (19287), 289 (6928), 295 (6794), 480 (11155), 490 (11823), 509 (8988), 523 (7329) nm; IR (KBr): 3450, 3130, 2930, 2975, 1770, 1640, 1600, 1455, 1410, 1300 cm$^{-1}$; $^1$H— and $^{13}$C—NMR (Tables 2 and 3); MS (CI, positive % intensity): 393 (70), 392 (100), 377 (15), 361 (20), 333 (5).

Acetylation of Spartanamicin B

Spartanamicin B (45 mg) was dissolved in pyridine (5 ml) and acetic anhydride (1.0 ml) and kept at room temperature in dark. The red solution of the compound in pyridine changed to yellow 5 minutes after the addition of acetic anhydride. The reaction mixture, yellow in color, after 72 hours, was evaporated to dryness by azeotroping with toluene at the rotary evaporator. The crude yellow product indicated as a mixture of two compounds by the TLC analysis TLC purification of this product gave two bands, one for the aglycone acetate and the other for natural products acetate.

Spartanamicin A

Orange amphorphous powder $C_{42}H_{51}O_{16}N$, mp. 174–176° C.; IR (KBr): 3510, 2980, 2950, 2830, 2780, 1740, 1645, 1602, 1450, 1400, 1320, 1215, 1005 $cm^{-1}$; UV (MeOH—$H_2O$, 95:5), ($\epsilon$): 525 (9334), 510 (10,628), 491 (13757), 460 (11111), 289 (9090), 257 (24632), 233 (46830) nm; $^1H$— and $^{13}C$—NMR see Tables 4 and 5; MS (FAB+ % intensity): 826.142 (M++H, 90), 393 (42), 309 (95).

TABLE 2.

$^1$H-NMR (300 MHz, $CDCl_3$) of Spartanamicin B.

| Chemical Shift ppm | Multiplicity J = Hz | Number of Protons | Assignment |
| --- | --- | --- | --- |
| 12.92 | s | 1 | phenol |
| 12.76 | s | 1 | phenol |
| 12.17 | s | 1 | phenol |
| 7.69 | s | 1 | 11-CH |
| 7.29 | d, J = 9.4 | 1 | 2-, 3-CH |
| 7.27 | d, J = 9.4 | 1 | |
| 5.56 | bs | 1 | |
| 5.30 | d, J = 2.4 | 1 | |
| 5.12 | 5, J = 6.4, 5.9 | 1 | |
| 5.08 | bs | 1 | |
| 4.62 | bs | 1 | |
| 4.59 | bs | 1 | |
| 4.54 | q, J = 6.2 | 2 | |
| 4.11 | s | 1 | 10-H |
| 3.78–3.69 | m | 2 | |
| 3.76 | s | 3 | $OCH_3$ |
| 2.59 | dd, J = 15.0, 5.3 | 1 | |
| 2.53 | m | 4 | |
| 2.35 | d, J = 14.9 | 1 | |
| 2.22 | bs | 7 | |
| 1.95 | m | 4 | |
| 1.80 | m | 2 | |
| 1.58 | m | 2 | |
| 1.38 | d, J = 6.7 | 3 | $CH_3$ |
| 1.34 | d, J = 6.1 | 3 | $CH_3$ |
| 1.22 | d, J = 6.4 | 3 | $CH_3$ |
| 1.15 | t, J = 7.3 | 3 | $CH_3$ |

TABLE 3.

$^{13}$C-NMR Chemical shifts for Spartanamicin B and its Aglycone and their tentative assignments.

| No. | Spartanamicin ppm | Aglycone, Spartanone ppm | Assignment |
| --- | --- | --- | --- |
| 1 | 6.67 | 6.68 | C-15 |
| 2 | 32.12 | 32.37 | C-14 |
| 3 | 34.26 | 34.72 | C-8 |
| 4 | 52.50 | 52.54 | C-22 |
| 5 | 57.08 | 56.62 | C-10 |
| 6 | 61.52 | 62.47 | C-9 |
| 7 | 70.59 | 71.70 | C-7 |
| 8 | 112.19 | 112.16 | |
| 9 | 112.36 | 112.36 | C-2, C-3, C-11 |
| 10 | 114.64 | 114.70 | |
| 11 | 120.29 | 120.75 | C-16, C-17 |
| 12 | 129.66 | 129.76 | |
| 13 | 130.00 | 130.29 | |
| 14 | 131.47 | 132.41 | C-18, C-19 |
| 15 | 132.67 | 132.97 | |
| 16 | 142.36 | 142.37 | C-20, C-21 |
| 17 | 157.69 | 157.88 | |
| 18 | 158.34 | 158.45 | C-1, C-4, C-6 |
| 19 | 162.20 | 161.16 | |
| 20 | 171.22 | 171.21 | C-13 |
| 21 | 186.56 | 185.54 | |
| 22 | 190.40 | 190.45 | C-5, C-12 |
| 23 | 14.75 | — | |
| 24 | 16.91 | — | C-6', C-6'', C-6''' |
| 25 | 17.83 | — | methyls |
| 26 | 27.59 | — | |
| 27 | 29.32 | — | |
| 28 | 33.48 | — | |
| 29 | 33.71 | — | |

TABLE 3.-continued $^{13}$C-NMR Chemical shifts for Spartanamicin B and its Aglycone and their tentative assignments.

| No. | Spartanamicin ppm | Aglycone, Spartanone ppm | Assignment |
| --- | --- | --- | --- |
| 30 | 43.27 | — | |
| 31 | 65.29 | — | |
| 32 | 66.72 | — | |
| 33 | 68.30 | — | |
| 34 | 70.52 | — | |
| 35 | 71.60 | — | |
| 36 | 71.72 | — | |
| 37 | 74.00 | — | |
| 38 | 82.93 | — | |
| 39 | 99.36 | — | C-i', C-1'', C-1''' |
| 40 | 100.04 | — | anomeric |
| 41 | 101.64 | — | |
| 42 | 210.09 | — | aliphatic ketone |
| Total number of carbons in product | | | = 42 |
| Total number of carbons in Aglycone | | | = 22 |
| Total number of carbons for 3 sugar residues | | | = 20 |

EXAMPLE 5

This Example shows the isolation and characterization of the aglycone and sugars from Spartanamicin A.

Spartanamicin A (50 mg) was treated with HCl in MeOH as in the case of sparatnamicin B. Purification and crystallization of the aglycone, referred to as spartanone, afforded a reddish amorphous powder (25 mg). This product was identical to the aglycone from spartanamicin B, in every respect.

Characterization of Sugars from Spartanamicins B and A

Spartanamicins B and A were separately treated with HCl in MeOH (as in the case of aglycone preparation) and the reaction mixture was purified by TLC to obtain the sugars and the aglycones. The sugars from both spartanamicin B and A have also been separately characterized by acid hydrolysis of the respective products using GC-MS. The results from spartanamicin B hydrolysis are shown in FIGS. 15 and 16A to 16D. The structures are as follows:

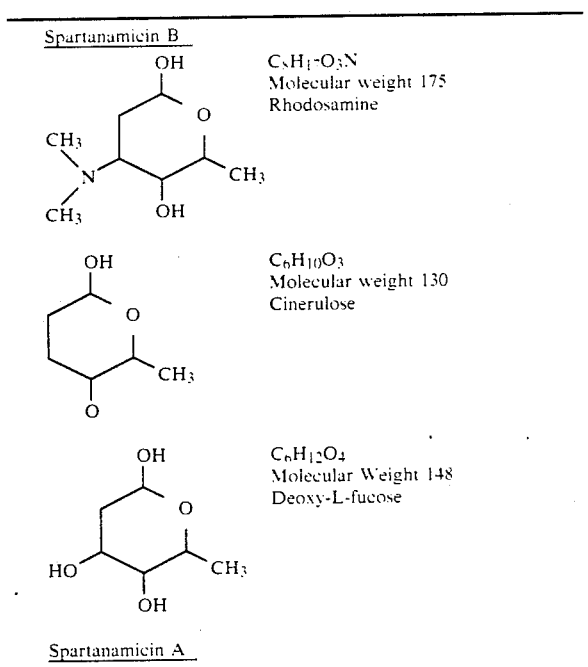

Spartanamicin B $C_8H_1-O_3N$
Molecular weight 175
Rhodosamine $C_6H_{10}O_3$
Molecular weight 130
Cinerulose $C_6H_{12}O_4$
Molecular Weight 148
Deoxy-L-fucose Spartanamicin A -continued

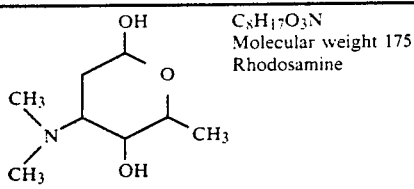

C₈H₁₇O₃N
Molecular weight 175
Rhodosamine

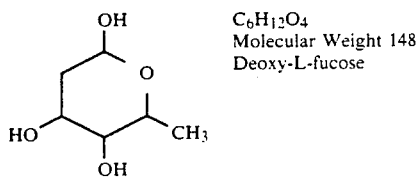

C₆H₁₂O₄
Molecular Weight 148
Deoxy-L-fucose

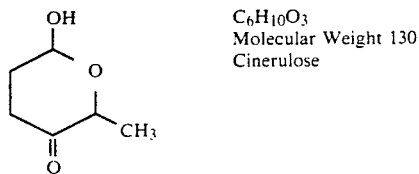

C₆H₁₀O₃
Molecular Weight 130
Cinerulose

Spartanamicin B, cinerulose and Deoxy-L-fucose are attached to rhodosamine as follows:

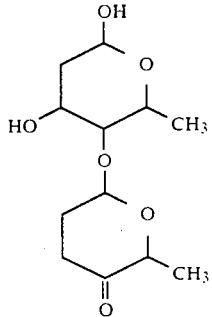

In spartanamicin A, these two sugars are connected to rhodosamine as follows:

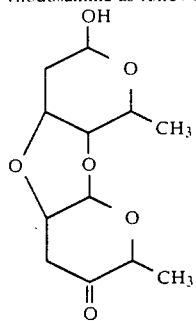

Structure of Spartanamicins A and B

Acid hydrolysis of spartanamicins A and B afforded the same aglycone, spartanone (Tables 3 and 4). The structure of aglycone is confirmed by spectral means. Mass spectral analysis of the aglycone (by FAB and CI) did not give a molecular ion at m/z 428 due to the aromatization of the ring D under MS condition. ¹H—NMR spectrum of spartanone indicated that there was no dehydration in ring D during the work up of the hydrolysis reaction.

Proton correlation spectroscopy of spartanamicin B clearly showed the correlation of the singlet aromatic proton at δ7.69 (H-11) to the proton at δ4.11 (H-10). The singlet proton at 4.11 ppm also couples to one of the C-8 protons appeared as a dd (J=5.2 and 15 Hz) at 2.35 ppm. There was no other coupling for this proton as evident from the COSY spectrum. Spartanamicin A showed an identical H-10 to H-11 and H-10 to H-8 correlation.

Comparison of the ¹H— and ¹³C—NMR spectra and mass spectra (FIGS. 9 to 14 for spartanamicins A and B) of the product and its aglycone suggested a 22-carbon aglycone and three sugar residues with a total of 20 carbons for both spartanamicin A and B. All three sugars contained a 2°-methyl groups each. The signal at 210 ppm, for an aliphatic ketone, and an amino group present in the product are assigned to the sugar residues. The aglycone did not contain the keto, 2°-methyl or the amino groups.

Spartanamicin B gave the molecular ion at m/z 828 (M⁺+H) and the HRMS indicated the MF as C₄₂H₅₃O₁₆N. The major fragments were at m/z 586 and 393. MS analysis of the aglycone also gave the highest mass peak at m/z 393. That is, the sugar free fragment of the product immediately aromatized under mass spectral conditions and is in agreement with the MS result of the aglycone. Collisionally Induced Dissociation (CID) of the molecular ion in the FAB (+) MS of spartanamicin B afforded daughter ions at m/z 698, 614, 586, 393, and 349. The important fragments at m/z 698 and 586 were generated by the loss of C₆H₁₀O₄ and C₆H₉O₂, deoxy-L-fucose and cinerulose fragments, respectively. HRMS analysis of the ion at m/z 586 gave the MF as C₃₀H₃₄O₁₂ (calcd: 586.2038; found: 586.2044). Loss of the sugar residue C₈H₁₄O₃ followed by two molecules of H₂O from the ion at m/z 586 gave the peak at m/z 393. This MS fragmentation pattern is a clear indication of the presence of C₈H₁₇O₃N, C₆H₁₀O₃, and C₆H₁₂O₄, as the three sugars in spartanamicin B.

Acetylation of the spartanamicin B in pyridine-Ac₂O at room temperature, the work up and purification afforded a triacetate of the aglycone and a tetra acetate of the natural product. Since the aglycone acetate obtained from the acetylation of the product had only three acetates, confirmed by NMR and MS, suggested that this triacetate is only a cleavage product of the product peracetate(s). It is also important to note the absence of the H-10 at 4.11 ppm in this acetate confirmed by ¹H—NMR spectrum. This can be explained by the dehydration between C-9 3° hydroxyl and C-10 proton. This was further confirmed by the m/z at 536 in its FAB (−) mass spectrum. Positive ion FAB MS of the triacetate gave the highest peak at m/z 519.

Spartanamicin A differs from spartanamicin B in two of the three sugar residues. Both compounds have the same aglycone and the cinerulose sugar portion. In spartanamicin A, the amino sugar has an N(CH₃)₂ group similar to spartanamicin B. The C₈-sugar (rhodosamine) in spartanamicin A is an amino sugar with an N(CH₃)₂ group, as in the case of aclacinomicin antibiotics.

Acid hydrolysis of both spartanamicins yielded the same aglycone. TLC verification of these hydrolyzed products indicated ninhydrin positive compounds, an indication of the presence of amino sugars. The other two sugars are detected by H₂SO₄ spray followed by charring at 110° C. These sugars were partially purified by TLC and confirmed by GC-MS or MS (FAB) analysis.

Other amino sugars which are hexoses besides daunosamine or rhodasamine can be present in compounds related to spartanamicin A and spartanamicin B. Such amino sugars are well known to those skilled in the art.

TABLE 4.

$^1$H-NMR (300 MHz, CDCl$_3$) assignments for Spartanone, Aglycone from Spartanamicin B and A.

| Chemical Shift ppm | Multiplicity J = Hz | Number of Protons | Assignment |
|---|---|---|---|
| 12.89 | s | 1 | phenol |
| 12.78 | s | 1 | phenol |
| 12.10 | s | 1 | phenol |
| 7.70 | s | 1 | 11-H |
| 7.30 | d, J = 9.4 | 1 | |
| 7.26 | d, J = 9.4 | 1 | 2-H & 3-H |
| 5.38 | d, J = 4.7 | 1 | 7-H |
| 4.11 | s | 1 | 10-H |
| 3.72 | s | 1 | OCH$_3$ |
| 2.56 | dd, J = 15.0, 5.2 | 1 | 8-H × 2 |
| 2.35 | dd, J = 14.9 | 1 | |
| 1.74 | qq, J = 7.3 | 1 | 14-H × 2 |
| 1.60 | qq, J = 7.2 | 1 | |
| 1.27 | bs | 2 | OH × 2 |
| 1.13 | t, J = 7.3 | 3 | 15-H × 3 |

TABLE 5.

$^{13}$C-NMR Chemical shifts for Spartanamicin A and its Aglycone and their tentative assignments.

| No. | Spartanamicin ppm | Aglycone, Spartanone ppm | Assignment |
|---|---|---|---|
| 1 | 6.69 | 6.68 | C-15 |
| 2 | 32.17 | 32.37 | C-14 |
| 3 | 33.74 | 34.72 | C-8 |
| 4 | 52.54 | 52.54 | C-22 |
| 5 | 57.15 | 56.62 | C-10 |
| 6 | 61.50 | 62.47 | C-9 |
| 7 | 71.68 | 71.70 | C-7 |
| 8 | 112.36 | 112.16 | |
| 9 | 112.52 | 112.36 | C-2, C-3 and C-11 |
| 10 | 114.80 | 114.70 | |
| 11 | 120.40 | 120.75 | |
| 12 | 129.73 | 129.76 | C-16, C-17 |
| 13 | 130.09 | 130.29 | |
| 14 | 131.49 | 132.41 | C-18, C-19 |
| 15 | 132.80 | 132.97 | |
| 16 | 142.44 | 142.37 | C-20, C-21 |
| 17 | 157.83 | 157.88 | |
| 18 | 158.42 | 158.45 | |
| 19 | 162.28 | 161.16 | C-1, C-4, C-6 C-13 |
| 20 | 171.31 | 171.21 | |
| 21 | 185.76 | 185.54 | |
| 22 | 190.62 | 190.45 | C-5, C-12 |
| 23 | 16.03 | — | |
| 24 | 16.18 | — | |
| 25 | 17.88 | — | CH$_3$ × 3, sugars |
| 26 | 26.97 | — | |
| 27 | 29.27 | — | |
| 28 | 39.73 | — | |
| 29 | 43.21 | — | |
| 30 | 62.98 | — | |
| 31 | 65.28 | — | |
| 32 | 66.91 | — | |
| 33 | 67.27 | — | |
| 34 | 68.28 | — | |
| 35 | 70.64 | — | |
| 36 | 74.13 | — | |
| 37 | 77.23 | — | |
| 38 | 77.93 | — | |
| 39 | 91.53 | — | |
| 40 | 99.07 | — | Anomeric, sugars |
| 41 | 101.59 | — | |
| 42 | 208.24 | — | Aliphatic ketone sugars |

Total number of carbons in product = 42
Total number of carbons in Aglycone = 22
Total number of carbons for 3 sugar residues = 20

TABLE 6.

Physicochemical Properties of Spartanamicin B.

| | |
|---|---|
| Nature: | Red-orange amorphous powder |
| Mol. Formula: | C$_{42}$H$_{53}$O$_{16}$N (HRFABMS) |
| Mol. Wt.: | 827 |
| Melting Point: | 159-161° C. |
| TLC* (Rf): | 0.41 ± 0.03 |
| HPLC** (RT): | 7.12 min |
| Solubility | Soluble in chloroform, carbon tetrachloride, toluene, ethyl acetate, N,N-dimethyl formamide (DMF), dimethyl sulfoxide (DMSO), acetone and glacial acetic acid Sparingly soluble in 1-butanol, ethanol, methanol, acetonitrile Insoluble in hexane, cyclohexane, water and 2N HCl (note: hydrolyses upon standing in 2N HCl) |
| UV-Vis (MeOH—H$_2$O): (95:5) | max (ε) 525.0 (sh) (7,431) 510.0 (sh) (9,028) 491.0 (11,837) 460.0 (sh) (9,555) 289.5 (7,166) 257.0 (19,375) 233.5 (39,545) |
| IR (KBr Pellet): | 3490, 2980, 2950, 2830, 2780, 1740, 1650, 1602, 1455, 1405, 1325, 1300, 1225, 1165, 1125, 1100, 1045, 1010, 960, 925, 810, 785, 760, cm$^{-1}$ |

*Plates: Silica Gel 60 F254 (10 cm × 20 cm, 250 um thickness); solvent system: chloroform-methanol (95:5); detection: UV at 366 nm.
**Column: Nova Pak C$_{18}$ (3.9 mm × 150 mm, Waters); solvent system: CH$_3$CN—H$_2$O—formic acid (63:35:2); flow rate: 1.5 ml/min; detection: UV-Vis at 490 nm.

TABLE 7.

Physicochemical Properties of Spartanamicin A.

| | |
|---|---|
| Nature: | Orange amorphous powder |
| Mol. Formula: | C$_{42}$H$_{51}$O$_{16}$N (HRFABMS) |
| Mol. Wt.: | 825 |
| Melting point: | 1.70-172° C. |
| TLC* (Rf): | 0.67 ± 0.02 |
| HPLC** (RT): | 10.37 min |
| Solubility | Soluble in chloroform, carbon tetrachloride, toluene, ethyl acetate, N,N-dimethyl formamide (DMF), dimethyl sulfoxide (DMSO), acetonitrile, acetone and glacial acetic acid Sparingly soluble in 1-butanol, ethanol, methanol Insoluble in hexane, cyclohexane, water and 2N HCl |
| UV-Vis (MeOH—H$_2$O): (95:5) | max (ε) 525.0 (sh) (9,334) 510.0 (sh) (10,628) 491.0 (13,757) 460.0 (sh) (11,111) 289.5 (9,090) 257.0 (24,632) 233.5 (46,830) |
| IR (Kbr Pellet): | 3510, 2980, 2950, 2830, 2780, 1740, 1645, 1602, 1450, 1400, 1320, 1295, 1215, 1160, 1120, 1095, 1045, 1005, 990, 960, 925, 805, 780, 755 cm |

*Plates: Silica Gel 60 F254 (10 cm × 20 cm, 250 um thickness); solvent system: chloroform-methanol (95:5); detection: UV at 366 nm.
**Column: Nova Pak C18 (3.9 mm × 150 mm, Waters); solvent system: CH$_3$CN—H$_2$O—formic acid (63:35:2); flow rate: 1.5 ml/min; detection: UV-Vis at 490 nm.

We claim:

1. A composition or compound selected from the group consisting of spartanamicin A and B, having the molecular formula C$_{42}$H$_{53}$O$_{16}$N with a molecular weight of 827 for spartanamicin B and molecular formula C$_{42}$H$_{51}$O$_{16}$N with a molecular weight of 825 for spartanmicin A, which is produced by and isolated from mycelium of *Micromonospora spartanea* ATCC 53803.

2. The composition of claim 1 in a composition removed from disrupted mycelium of *Micromonospora spartanea* ATCC 53803 with a solvent for the compound which is a non-solvent for the mycelium.

3. The composition of claim 2 wherein the solvent used for the removal of the composition is trichloromethane in admixture with methanol.

4. The composition of claim 3 wherein the solvent is removed from the composition to produce a dry powder.

5. The composition of claim 4 wherein the powder has been dissolved in trichloromethane and methanol and impurities removed by chromatography using a column to produce the composition in substantially pure form.

6. The composition of claim 5 wherein the column is asilica column and wherein the two compounds have been separated from the composition with thin layer chromatography as compounds in pure form.

7. A compound having a formula selected from the group consisting of $C_{42}H_{53}O_{16}N$ with a molecular weight of 827 and referred to as spartanamicin B and $C_{42}H_{51}O_{16}N$ with a molecular weight of 825 and referred to as spartanamicin A and each compound having an aglycone of the formula:

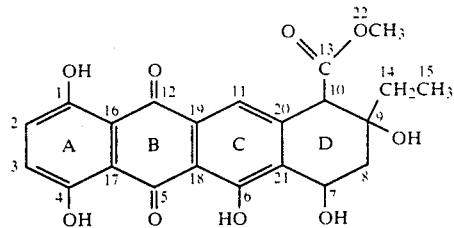

upon hydrochloric acid hydrolysis in methanol and for spartanamicin B sugar residues of rhodosamine, cinerulose and deoxy-L-fucose and for spartanamicin A sugar residues of deoxy-L-fucose, rhodosamine and cinerulose by gas chromatograph mass spectroscopy and the same sugar residues upon collisionally induced disassociation of spartanamicin A and B using mass spectroscopy.

8. The compound of claim 1 which is spartanamicin B.

9. The compound of claim 7 which is spartanamicin B.

10. THe compound of claim 1 which is spartanamicin A.

11. The compound of claim 7 which is spartanamicin A.

* * * * *

UNITED STATES PATENT AND TRADEMARK OFFICE
CERTIFICATE OF CORRECTION

PATENT NO. : 5,013,549

DATED : May 7, 1991

INVENTOR(S) : Alan R. Putnam, Saroj K. Mishra and Muraleedharan G. Nair

It is certified that error appears in the above—identified patent and that said Letters Patent is hereby corrected as shown below:

Column 4, line 13, "Tr aty" should be --Treaty--.

Column 4, line 50, after "the" and before "YMG", the following should be inserted --laboratory media, but its growth is particularly good on--.

Column 5, line 5, after "xanthine", a period --.-- should be inserted.

Column 6, line 23, "10 g/l)" and "4 g/l)" should read
--(10 g/l)-- and --(4 g/l)--, respectively.

Column 7, line 54, the following paragraph should be inserted after "Table 1.",
--Table 1
Minimum inhibitory concentration of Spartanamycin-B against certain bacteria and fungi. (The substance was dissolved in DMSO, 20 ul of the solution was mixed with two ml of liquid Emmons medium containing ca 10,000 Colony forming Units of fungal test strains or 100,000 CFU's of bacterial test strains).--

UNITED STATES PATENT AND TRADEMARK OFFICE
CERTIFICATE OF CORRECTION

PATENT NO. : 5,013,549
DATED : May 7, 1991
INVENTOR(S) : Alan R. Putnam, Saroj K. Mishra and Muraleedharan G. Nair It is certified that error appears in the above—identified patent and that said Letters Patent is hereby corrected as shown below:

Column 7, lines 66 and 68, "08" should be --0.8--.

Column 8, line 5, "04" should be --0.4--.

Column 8, line 43, "n HCl" should be --in HCl--.

Column 9, line 67, "29.32" should be --29.21--.

Column 14, line 27, "(10 cm . 20 cm" should be --10 cm x 20 cm--.

Column 14, line 29, "3.9 mm . 150 mm" should be --3.9 mm x 150 mm--.

Column 14, line 67, "spartanmicin A" should be --spartanamicin A--.

Signed and Sealed this

Twenty-third Day of February, 1993

Attest:

STEPHEN G. KUNIN

Attesting Officer      Acting Commissioner of Patents and Trademarks